United States Patent
Say et al.

[11] Patent Number: 6,117,290
[45] Date of Patent: Sep. 12, 2000

[54] SYSTEM AND METHOD FOR MEASURING A BIOANALYTE SUCH AS LACTATE

[75] Inventors: James L. Say, Alameda, Calif.; Nathan R. Long, Ada, Mich.; Eric A. Peper, Lincoln, Nebr.; Henning Sakslund, Pleasant Hill, Calif.

[73] Assignee: Pepex Biomedical, LLC, Villa Park, Calif.

[21] Appl. No.: 09/122,496

[22] Filed: Jul. 24, 1998

Related U.S. Application Data

[60] Provisional application No. 60/060,142, Sep. 26, 1997.

[51] Int. Cl.[7] .................................................. G01N 27/26
[52] U.S. Cl. ..................... 204/403; 204/409; 422/82.01; 604/181
[58] Field of Search .................... 204/403, 400, 204/409; 422/82.01, 82.05; 604/181, 187, 218

[56] References Cited

U.S. PATENT DOCUMENTS

| | | |
|---|---|---|
| D. 354,347 | 1/1995 | Knute et al. . |
| D. 354,559 | 1/1995 | Knute et al. . |
| 3,948,604 | 4/1976 | Hoppesch ................................. 422/84 |
| 4,573,968 | 3/1986 | Parker . |
| 4,640,821 | 2/1987 | Mody et al. ............................... 421/81 |
| 4,734,184 | 3/1988 | Burleigh et al. ........................ 204/409 |
| 4,919,649 | 4/1990 | Timothy et al. ........................... 604/65 |
| 4,995,867 | 2/1991 | Zollinger ................................. 604/514 |
| 5,004,583 | 4/1991 | Guruswamy ............................... 422/58 |
| 5,165,406 | 11/1992 | Wong . |
| 5,220,920 | 6/1993 | Gharib . |
| 5,243,982 | 9/1993 | Möstl et al. ............................. 600/316 |
| 5,264,105 | 11/1993 | Gregg et al. . |
| 5,271,815 | 12/1993 | Wong . |
| 5,330,634 | 7/1994 | Wong et al. ......................... 205/777.5 |
| 5,384,028 | 1/1995 | Ito .......................................... 204/403 |
| 5,431,174 | 7/1995 | Knute . |
| 5,505,828 | 4/1996 | Wong et al. . |
| 5,512,159 | 4/1996 | Yoshioka et al. ........................ 204/403 |
| 5,609,749 | 3/1997 | Yamauchi et al. ................... 205/777.5 |

FOREIGN PATENT DOCUMENTS

| | | |
|---|---|---|
| 0 256 415 | 2/1988 | European Pat. Off. . |
| 0 327 658 | 8/1989 | European Pat. Off. . |
| 0 420 296 A1 | 4/1991 | European Pat. Off. . |
| WO 96/22730 | 8/1996 | WIPO . |

*Primary Examiner*—Jill Warden
*Assistant Examiner*—Alex Noguerola
*Attorney, Agent, or Firm*—Merchant & Gould P.C.

[57] ABSTRACT

The present disclosure relates to an on-line lactate sensor arrangement. The sensor arrangement includes a lactate sensor, a catheter for withdrawing a test sample, and a first fluid flow line provided fluid communication between the lactate sensor and the catheter. The sensor arrangement also includes a source of sensor calibration and anticoagulant solution, and second fluid flow line providing fluid communication between the source of sensor calibration and anticoagulant solution and the lactate sensor.

39 Claims, 15 Drawing Sheets

VALVE IN NORMALLY CLOSED POSITION - VACUUM OFF

VALVE IN OPEN POSITION - VACUUM ON

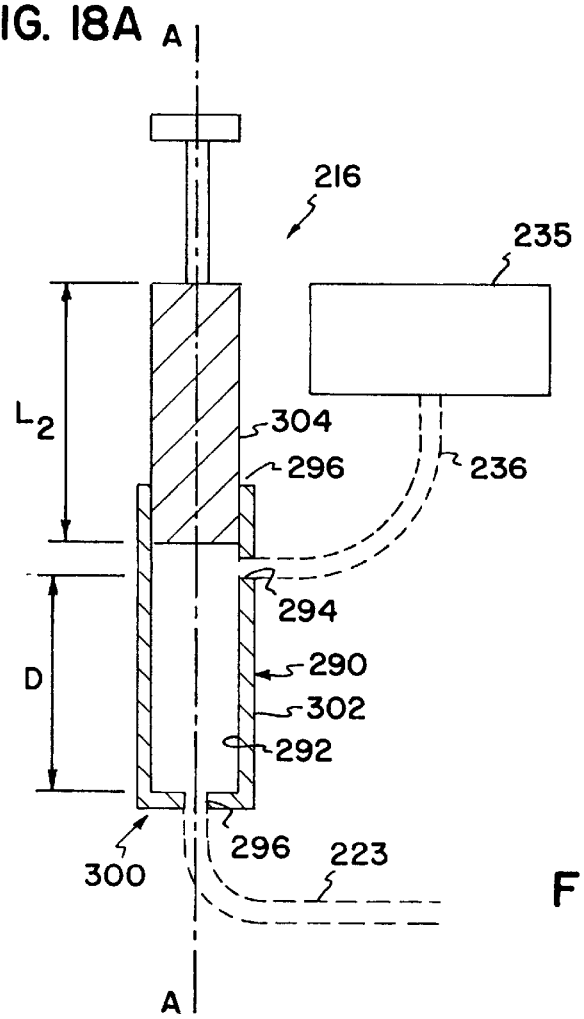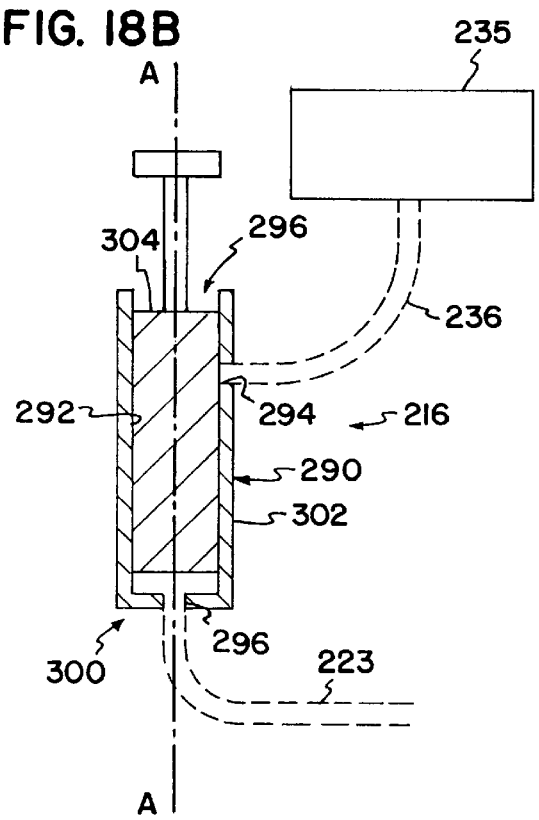

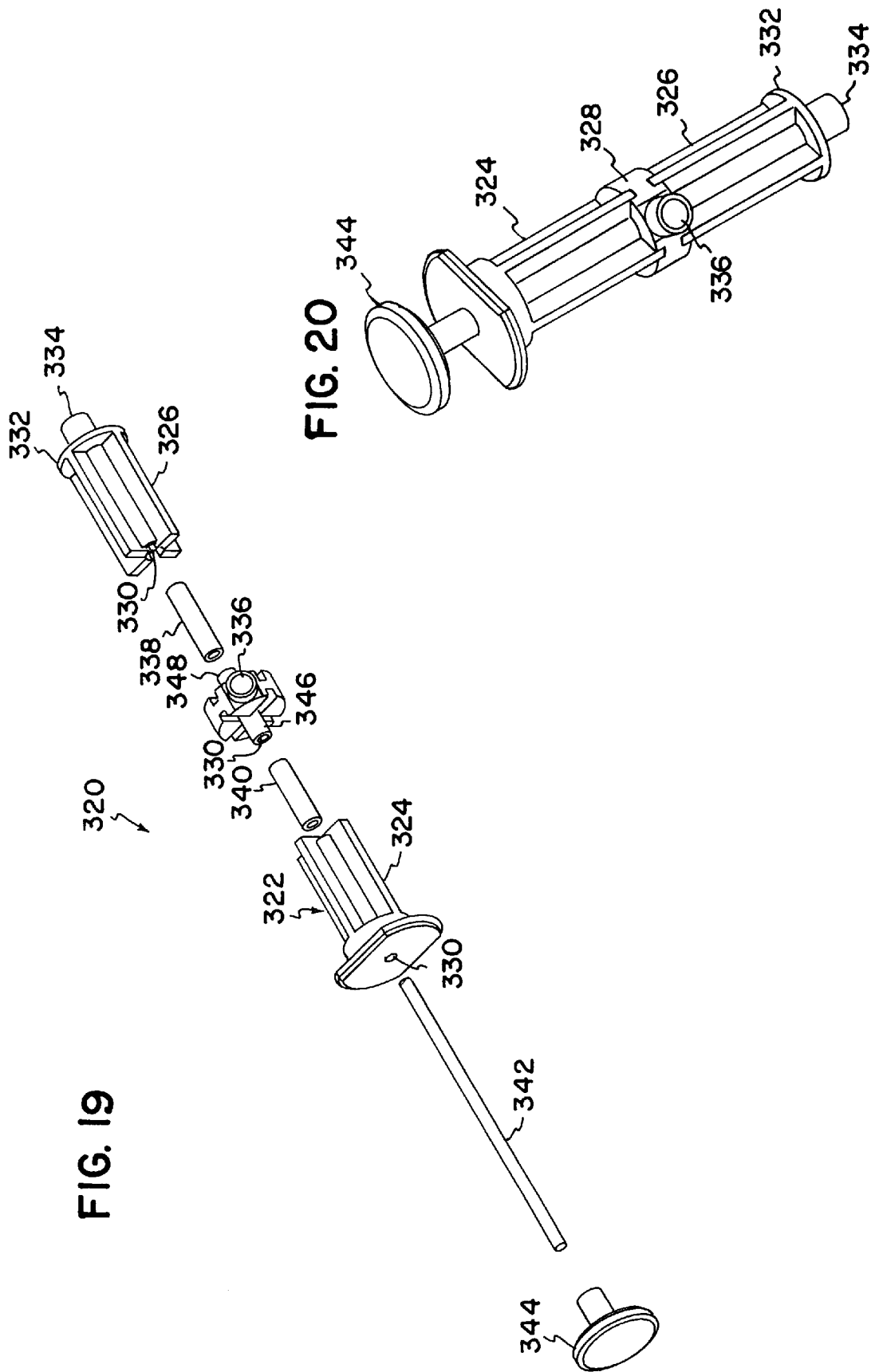

SYSTEM AND METHOD FOR MEASURING A BIOANALYTE SUCH AS LACTATE

CROSS REFERENCE TO RELATED APPLICATION

This application claims priority to United States Provisional Application Ser. No. 60/060,142, filed Sep. 26, 1997.

FIELD OF THE INVENTION

This invention relates generally to systems and methods for measuring bioanalytes. More particularly, the present invention relates to systems and methods for measuring lactate.

BACKGROUND OF THE INVENTION

For critical care patients, physicians have long relied on personal examination and clinical laboratory results to determine the presence and concentration of biological analytes in a patient. Clinical laboratories offer a wide range of automated systems for high-volume testing and analytical support in a well controlled, high quality environment. However, clinical laboratories can not provide the immediate results needed to properly treat trauma and multi organ dysfunction/failure patients.

To meet the clinical need for immediate test results, several technologies are emerging for testing using reliable, automated analyzers at the patient's bedside. This type of testing is commonly termed point-of-care (POC) diagnostic testing. POC diagnostic test systems include electrochemical biosensors, optical fluorescence sensors, paramagnetic particles for coagulation test systems, and micromachined devices for both chemical and immunochemical testing. These technologies have allowed multi-analyte chemistry panels to be performed rapidly and have addressed previous obstacles such as calibration of test devices. POC tests can be classified as: 1) in vitro, which is performed at the bedside; 2) ex vivo or para vivo, which is performed at wrist-side; and 3) in vivo, which is performed inside the patient. POC tests offer indirect cost efficiencies and savings such as reduced labor costs, decreased blood identification and transport errors, and reduced patient complications.

In vitro or bedside POC devices are used typically in several departments of the hospital including intensive care units; operating rooms; emergency departments (ER); interventional departments; general patient care departments; and outpatient surgery and ambulatory care units. In vitro POC diagnostic tests offer a wide range of diagnostic tests, similar to the clinical laboratory. In vitro POC diagnostic test systems typically are not connected on-line to the patient and require an operator for blood sampling. Key categories of diagnostic test in the POC diagnostic market include arterial blood gases, blood chemistries, blood glucose, coagulation, drugs-of-abuse testing, hemoglobin, hematocrit, infectious diseases, and therapeutic drug monitoring. Other categories include cancer markers, cardiac markers, cholesterol detection, immunodiagnostics, infectious disease detection, lactate, and thrombolytic monitoring.

Ex vivo POC diagnostics use external sensors for on-line real-time testing with little to no blood loss. Typically, sampled blood flows through a closed system to minimize blood contact. Ex vivo POC systems minimize problems associated with in vivo sensors, including clotting, inaccuracy, calibration drift, and an inability to recalibrate once in the patient. Optical Sensors, Inc. of Minneapolis, Minn. currently markets ex vivo blood gas analyzers which utilize a hand operated syringe system. VIA Medical Corporation of San Diego, Calif. markets ex vivo blood glucose analyzers which utilize a relatively large volume, automated sampling and analysis system. U.S. Pat. No. 5,505,828 discloses an exemplary ex vivo POC system.

In vivo POC diagnostics offer considerable potential in the treatment of most critical and unstable patients. Although many companies are developing in vivo sensors, technical hurdles have thus far kept in vivo sensors from common commercial use.

Ex vivo and in vivo POC diagnostics, since they are on-line systems, can reduce quality control and information integration errors that occur with clinical or in vitro POC tests. Quality control errors are commonly due to operator errors, not instrument errors or device failures. Exemplary errors include inappropriate specimen volume, inaccurate calibration, use of deteriorated test strips, inadequate validation, insufficient instrument maintenance, bad timing of the test procedure, and use of the wrong materials. Clinical information system integration allows test data collected at the bedside to be put directly into the patient record. This improves the efficiency of the patient management process, allowing the integration of the laboratory's information system and clinical information systems, providing a "seamless" flow of all types of patient information.

SUMMARY OF THE INVENTION

One aspect of the present invention relates to an on-line lactate sensor arrangement. The sensor arrangement includes a lactate sensor, a first flow line for withdrawing a fluid sample from a patient, and a source of sensor calibration fluid. The first fluid flow line conveys the fluid sample from the patient to the lactate sensor. A second fluid flow line provides fluid communication between the source of calibration fluid and the lactate sensor.

Another aspect of the present invention relates to a sensor arrangement including a sensor and a pump device for controlling fluid flow past the sensor. The pump device includes a housing defining a piston chamber. A piston is reciprocally mounted within the chamber. The housing defines first and second ports that provide access to the piston chamber. The first port is axially spaced from the second port. The arrangement also includes a first fluid flow line providing fluid communication between the sensor and a sample fluid, and a second fluid flow line providing fluid communication between the second port of the housing and the sensor. The sensor arrangement further includes a source of calibration fluid including calibrate for calibrating the sensor. The source of calibration fluid is in fluid communication with the first port of the housing.

An additional aspect of the present invention relates to a fluid control device. The fluid control device includes a housing that defines a piston chamber. The housing also defines first and second ports that provide access to the piston chamber. The first port is axially spaced from the second port. The fluid control device further includes a piston arranged and configured to be axially reciprocated within the piston chamber.

A further aspect of the present invention relates to a method for on-line measurement of lactate. The method includes the step of withdrawing a sample fluid from a mammal through a first fluid flow line such as a catheter. The method also includes the step of conveying the sample fluid through the first fluid flow line past a lactate sensor. The method further includes the step of measuring an amount of lactate in the fluid sample with the sensor.

Still another aspect of the present invention also relates to a method for on-line measurement of lactate. The method includes the step of providing a sensor arrangement including a catheter, a lactate sensor, a source of calibration fluid, a first flow line extending between the catheter and the lactate sensor, and a second flow line extending between the lactate sensor and the source of calibration fluid. The method also includes the step of conveying the calibration fluid at a predetermined rate from the source of calibration fluid, through the second flow line, past the sensor, and into the first flow line. The method further includes the step of calibrating the sensor as the calibration fluid flows past the sensor. The method additionally includes the step of reversing the flow of calibration fluid in the first and second flow lines and conveying a sample fluid from the catheter, through the first flow line, past the sensor, and into the second flow line. Finally, the method includes the step of measuring an amount of lactate in the sample fluid as the sample fluid flows past the lactate sensor.

An additional aspect of the present invention relates to a sensing system including an analyte sensor, a catheter for drawing a fluid sample from a patient, and a first fluid flow providing fluid communication between the catheter and the analyte sensor. The system also includes a source of sensor calibration fluid, a second fluid flow line providing fluid communication between the source of sensor calibration fluid and the analyte sensor, and means for drawing a fluid sample through the catheter and past the sensor at a flow rate less than 100 microliters per minute.

A further aspect of the present invention relates to an on-line sensing system including a sensor and a manifold including a first port and a second port. The manifold defines a first flow path providing fluid communication between the first port and the sensor, and a second flow path providing fluid communication between the second port and the sensor. The system also includes a plurality of resilient diaphragms for opening and closing flow through the first and second flow paths. A pneumatic valve actuator pneumatically causes the resilient diaphragms to open and close flow through the first and second flow paths. A sample line provides fluid communication between the first port and a sample fluid, and a calibrant line provides fluid communication between the second port and a source of calibrant fluid.

These and various other features which characterize the invention are pointed out with particularity in the attached claims. For a better understanding of the invention, it's advantages, and objectives obtained by its use, reference should be made to the drawings and to the accompanying description, in which there is illustrated and described preferred aspects of the present invention.

BRIEF DESCRIPTION OF THE DRAWINGS

The accompanying drawings, which are incorporated in and constitute a part of this specification, illustrate several aspects of the invention and together with the description, serve to explain the principles of the invention. A brief description of the drawings is as follows:

FIG. 18A is a schematic view of an embodiment of a pump device suitable for use with the system of FIG. 10, the pump device is shown in a retracted position;

FIG. 18B schematically shows the pump device of FIG. 18A in an extended position;

FIGS. 19 is an exploded view of a preferred pump device constructed in accordance with the principles of the present invention; and FIG. 20 is an assembled perspective view of the pump device of FIG. 19.

DETAILED DESCRIPTION OF THE PREFERRED EMBODIMENT

Reference will now be made in detail to exemplary aspects of the present invention which are illustrated in the accompanying drawings. Wherever possible, the same reference numbers will be used throughout the drawings to refer to the same or like parts.

An aspect of the present invention relates to systems and methods for providing on-line monitoring/measurement of bioanalytes in a patient. One particular aspect of the present invention relates to systems and methods for providing on-line measurement of lactate concentrations in a patient.

Lactate is a small molecule that is produced by all tissues and organs of a patient's body that are in "distress". Wherever in the patient's body the demands for oxygen exceed the supply, then a state of low perfusion exists and lactate is produced. For example, lactate is produced if a patient is bleeding, if a patient's heart is failing, if a person's limb is in danger of being lost, or if a person is not getting enough oxygen to breathe. Thus many life and limb threatening clinical states produce elevated blood lactate levels, even in the face of adequate oxygen delivery to the patient. It is a matter of oxygen supply and metabolic demand.

At the cellular level, lactate is inversely proportional to the vital cellular energy stores of adenosine triphosphate and is produced within six seconds of inadequate perfusion or cellular injury. It is thus an ideal biochemical monitor of cellular viability at the tissue level, and of patient viability at the systemic level.

Clinically, the dire significance of elevated and rising blood lactate values is known. Trauma physicians and clinical evidence support the hypothesis that a simple, inexpensive, continuous, monitor of lactate in the trauma setting, will save lives by providing timely, life-saving information that will help dictate triage and therapy. For example, an emergency room patient who has a blood lactate level of 4 mM has a 92% mortality rate within the next 24 hours. If this level is 6 mM, then the mortality rate rises to 98%. In animal experiments, blood lactate levels begin to rise within minutes of hemorrhage, and conversely, begin to fall just as quickly with adequate resuscitation. In multivariate analysis, blood lactate is the best indicator of the degree of shock (superior to blood pressure, heart rate, urine output, base deficit, blood gas and Swan-Ganz data) and is proportional to the shed blood volume. Blood lactate levels correlate with a trauma patient's chances of survival. Therapy that fails to control a patient's increasing lactate levels must be modified or additional diagnoses quickly sought.

Figure 1:
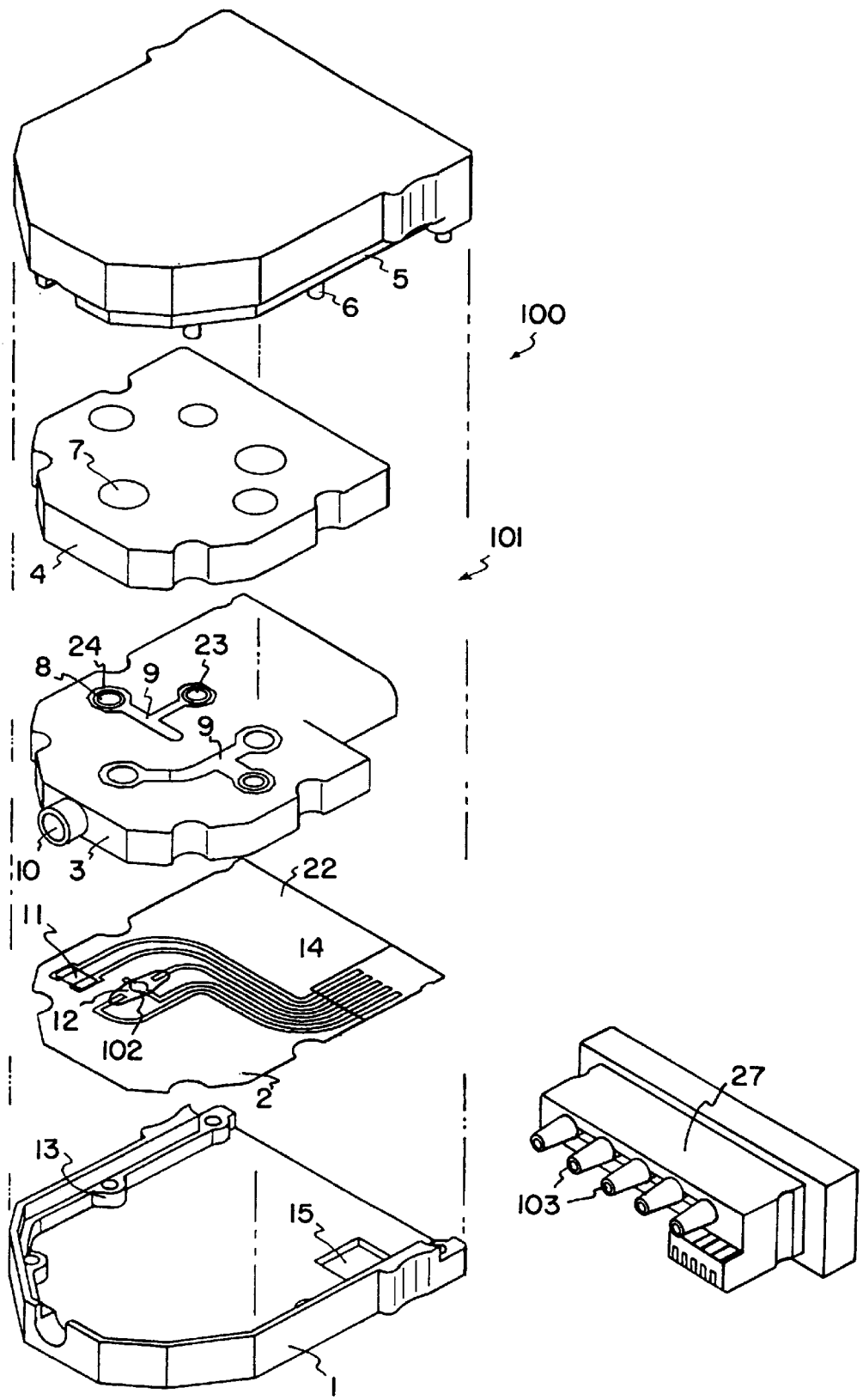
FIG. 1 is an exploded perspective view of one embodiment of a sensor module, according to the present invention.

FIG. 1 shows an assembly 100 suitable for providing on-line monitoring/measurement of bioanalytes such as lactate in a patient. The assembly 100 includes a molded polymer shell having a bottom half 1 and a top half 5 adapted for housing the various components of the device 101. The device 101 includes an array of valves, integrated with a manifold element in a printed circuit subassembly. The components are generally planar and are assembled as a stack sequence of five components.

Still referring to FIG. 1, the assembly 100 is depicted as including a fluid manifold plate 3, a pneumatic valve actuator 4, a printed flex circuit subassembly 2, top shell 5, bottom shell 1, and input/output connector terminal 27.

The bottom shell 1 provides support for each of the internal components. Interior profile 13 provides proper alignment of the component stack. Recess 15 allows printed circuit assembly 2 to recess into the shell 1.

Printed flex circuit subassembly 2 provides an electrical connection between the input output connector terminal 27, a lactate sensor site 12, and a temperature sensor 11. Conductive traces 14 are printed with a dielectric coating 22 of defined thickness. This coating is patterned to create a flow chamber 102 around the lactate sensor site 12. Flow chamber 102 has no dielectric coating. An adhesive coating patterned similarly to the dielectric coating 22 and applied over the dielectric coating 22 effects a fluid seal with the fluid manifold plate 3 and further defines the flow chamber 102.

Figure 2:
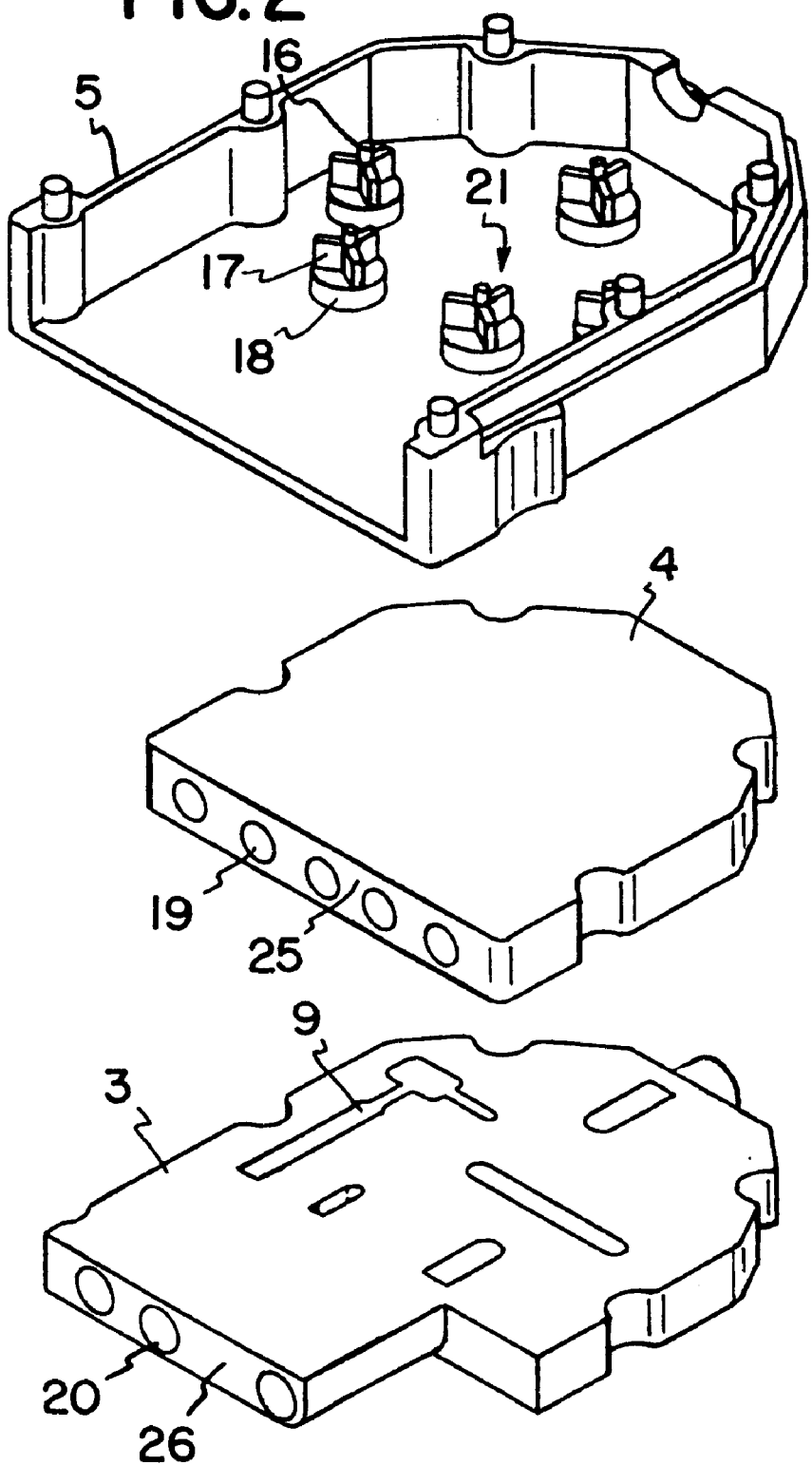
FIG. 2 is an exploded perspective view of a subassembly of the sensor module depicted in FIG. 1, according to the present invention.

In reference now to FIGS. 1 and 2, the fluid manifold plate 3 creates flow paths through the assembly 100. The manifold plate 3 preferably is an injection molded polymer structure having a pattern of channels 9 on opposing top and bottom surfaces. These channels are linked by annular passages 20, FIG. 2, that pierce the body of the fluid manifold plate 3 at an axis orthogonal to the channels 9. The combination of channels 9 and annular passages 20 serves two functions. Some function as connective passageways to direct fluid from one face of the fluid manifold plate 3 to the other. Others terminate on the top surface of the fluid manifold plate 3 in a manner that forms one element of a valve structure 23. As described further below, the valve structure 23 controls fluid flow through the assembly 100.

Figure 5:
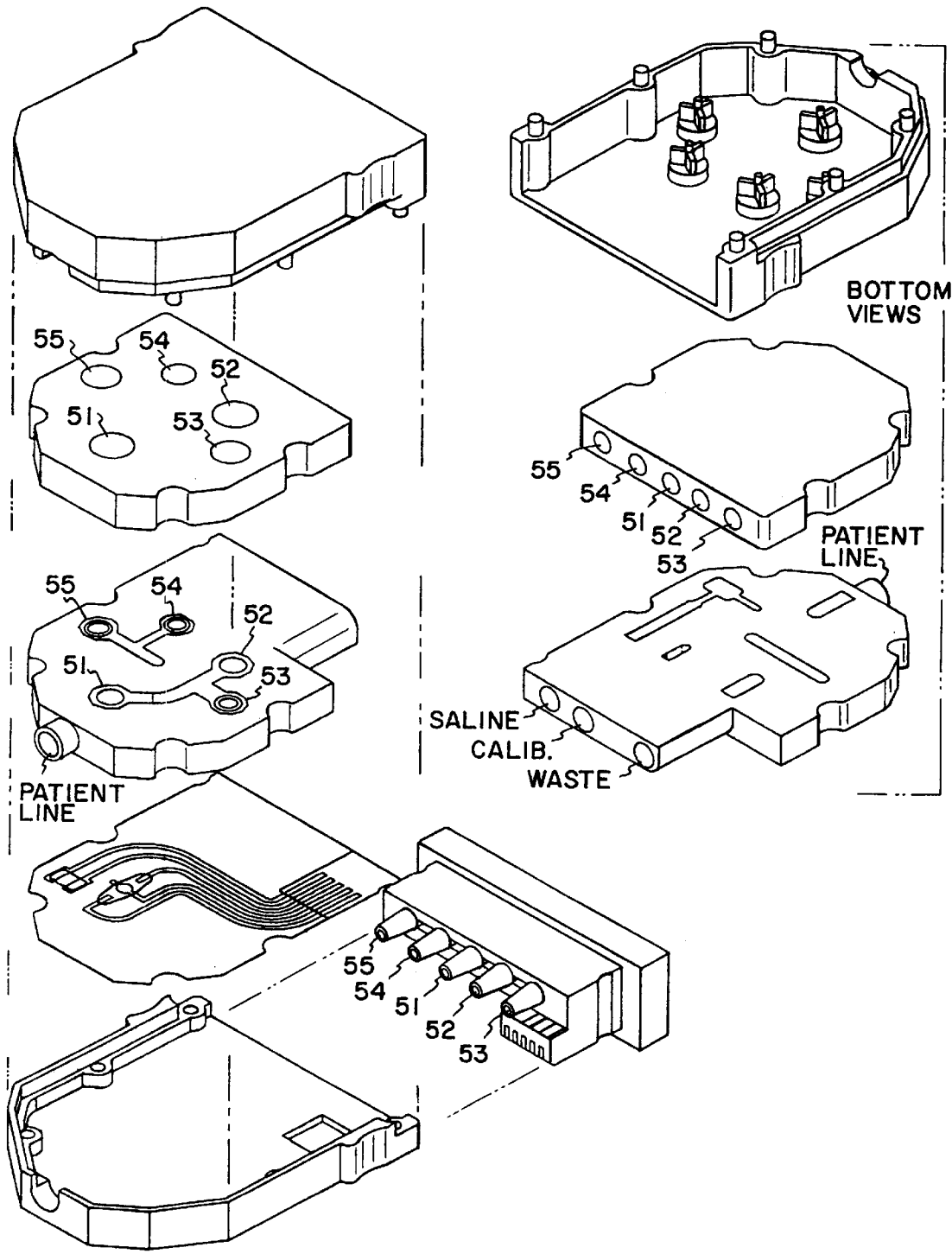
FIG. 5 is an exploded perspective view of the sensor module, analogous to FIGS. 1 and 2 and showing functional aspects of the sensor.

In reference now to FIG. 5, three ports adapted for connection to external fluid lines are shown. A first port 60 (labeled saline) is adapted for connection to a patient infusate bag. A second port 62 (labeled waste) is adapted for connection to a waste bag. A third port 64 (labeled calib) is adapted for connection to a calibration/anticoagulant bag. A line to the waste bag preferably contains a check valve to prevent backflow. A line to the calibration bag preferably contains a reversible fluid pump capable of at least two speeds of operation.

FIGS. 6–9 schematically depict the flow paths created by the valves, channels, and annular passages. Valve 52 controls outflow from assembly 100 to the patient. Valve 53 controls flow of the fluid in the patient line into either the sensor line or the shunt. Valve 54 controls flow from a calibration/anticoagulant bag 70 into the assembly 100. Valve 55 controls the shunt line that allows fluid to bypass the sensor 12.

In reference again to FIGS. 1 and 2, the pneumatic valve actuator 4 comprises either LIM or injection molded elastomer. It has a pattern of cylindrical chambers 7. The number of cylindrical chambers 7 is equal to the number of valves in the device. These cylindrical chambers pierce the pneumatic valve actuator 4 from the top face to the bottom face. The terminus of the chamber at the bottom face of the pneumatic valve actuator 4 is closed by a membrane 28, FIGS. 3–4. The membrane 28 is held in contact with the valve structure 24 by a pressure compensating structure 21. Membrane 28 acts to seal annular seat 8. Fluid flow is thus prevented until the valve is actuated by the application of a vacuum. A connecting lateral opening 19 extends from the cylindrical chamber 7 out to surface 25.

Referring again to FIG. 1, the input output connector terminal 27 provides a means of connecting vacuum lines and a remote monitor to the assembly 100. The input output connector terminal 27 attaches to the pneumatic valve actuator 4 at surface 25, FIG. 2. Tubing (not shown) attaches to the nipples 103 on the input output connector terminal 27. The tubing runs to 5 microprocessor controlled solenoid valves.

Opening a solenoid valve creates a vacuum gradient within the corresponding cylindrical chamber 7. This vacuum causes membrane 28, FIG. 3, to flex inwardly (FIG. 4) and break the seal between the membrane 28 and annular seat 8.

Figure 3:
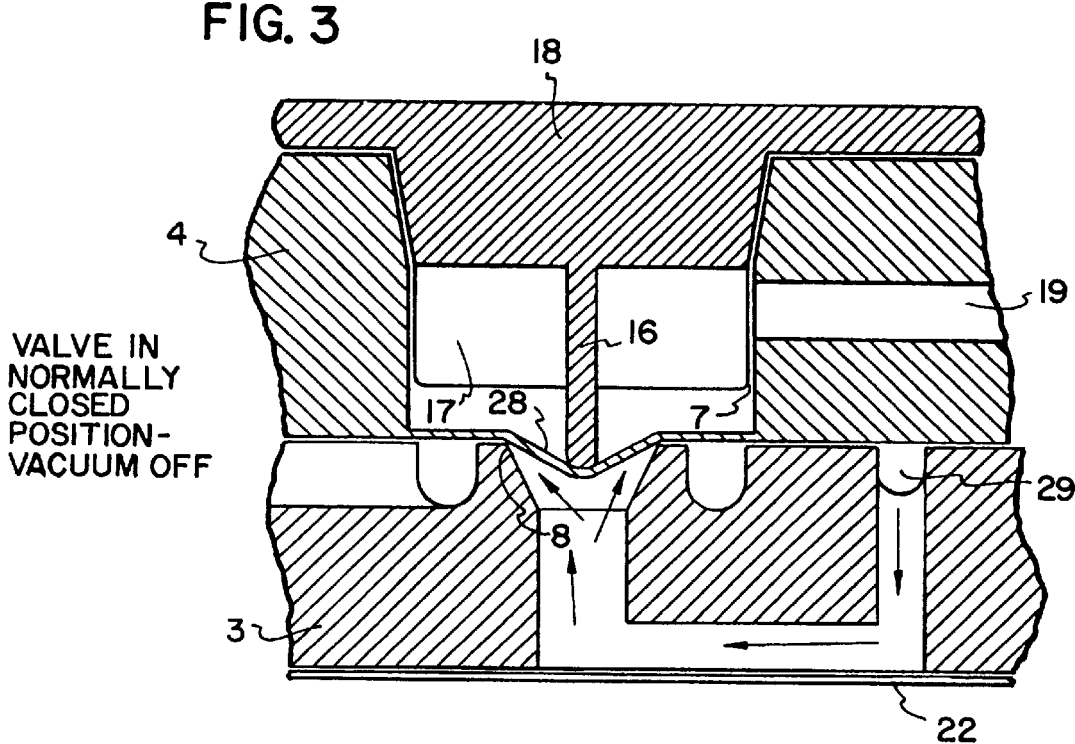
FIG. 3 is a schematic, cross-sectional view of a valve assembly of the sensor module in a closed position, according to the present invention.
Figure 4:
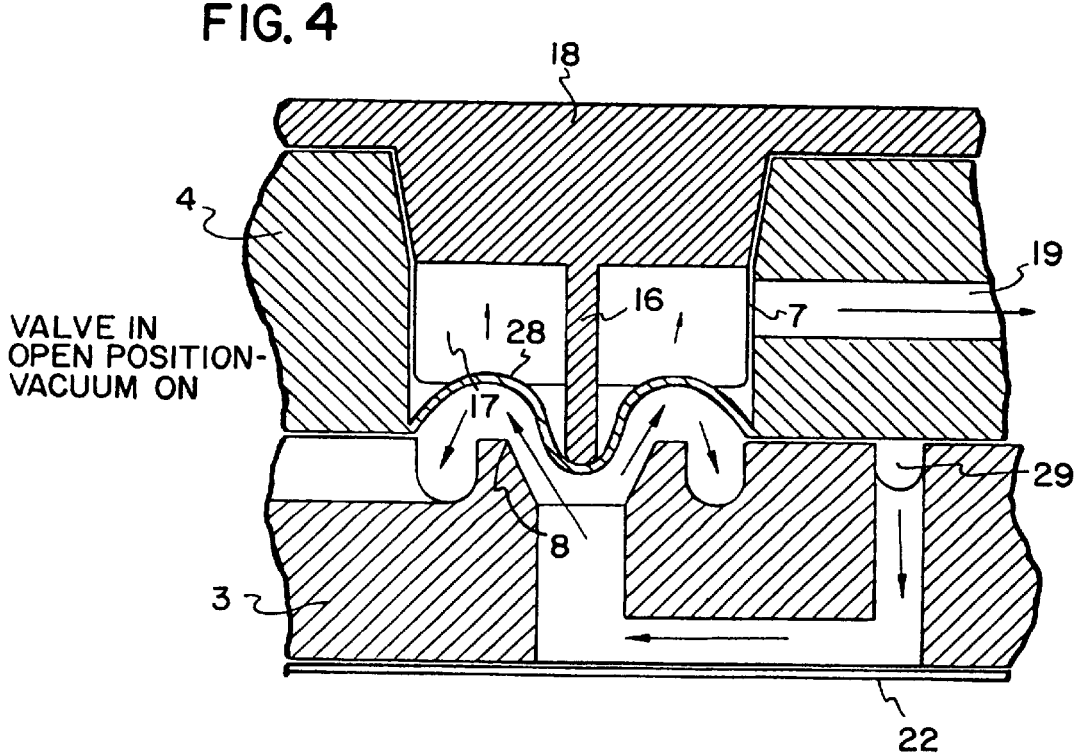
FIG. 4 is a schematic, cross-sectional view analogous to FIG. 3, depicting the valve assembly in an open position.

Again referring to FIGS. 1 and 2, the top shell 5 is preferably comprised of injection molded polymer. It mates with bottom shell 1 to contain the entire device 101. Raised profiles 6 allow an interference fit between top shell 5 and bottom shell 1. Pressure compensating structures are located at positions that correspond with the positions of the cylindrical chamber 7 and valve structures 24. These structures extend into the cylindrical chamber 7 and displace membrane 28 against the annular seat 8 (FIGS. 3–4).

The pressure compensating structure 21 comprises the following elements: A central pin 16 has three or more standing walls 17 radiating from it. A tapered boss 18 is located at the upper terminus of pressure compensating structure 21. The tapered boss 18 provides a surface for sealing and alignment between the cylindrical chamber 7 and top shell 5. The pressure compensating structure 21 functions to provide a bias load against a specified fluid back pressure. The pressure to crack the valve may be defined by varying the thickness of the membrane 28 the chamber 7, or the length of the central pin 16.

In operation, the assembly 100 is mounted on a patient's arm within about 25 cm of the injection site. A luer connection is made with the catheter connecting a bonded tubing extending from the connector 10. The input output connector 27 is plugged into the socket of pneumatic valve actuator 4. This makes a connection with the output of the printed circuit subassembly 2 and the five pneumatic ports common to surface 25.

Figure 6:
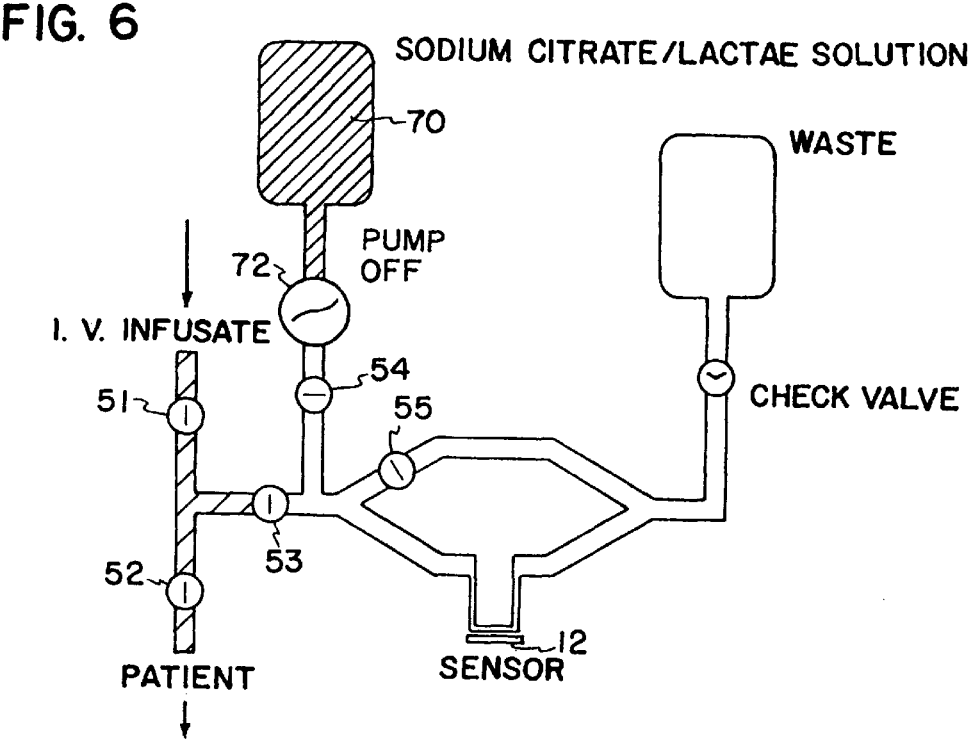
FIGS. 6–9 are schematic diagrams illustrating the sensor module in various modes of operation.

FIG. 6 depicts a patient being infused with saline. Vacuum is applied to open valves 51 and 52. Valves 53, 54, and 55 are closed. Fluid pump 72 is off. This state results in saline flow to the patient.

Figure 7:
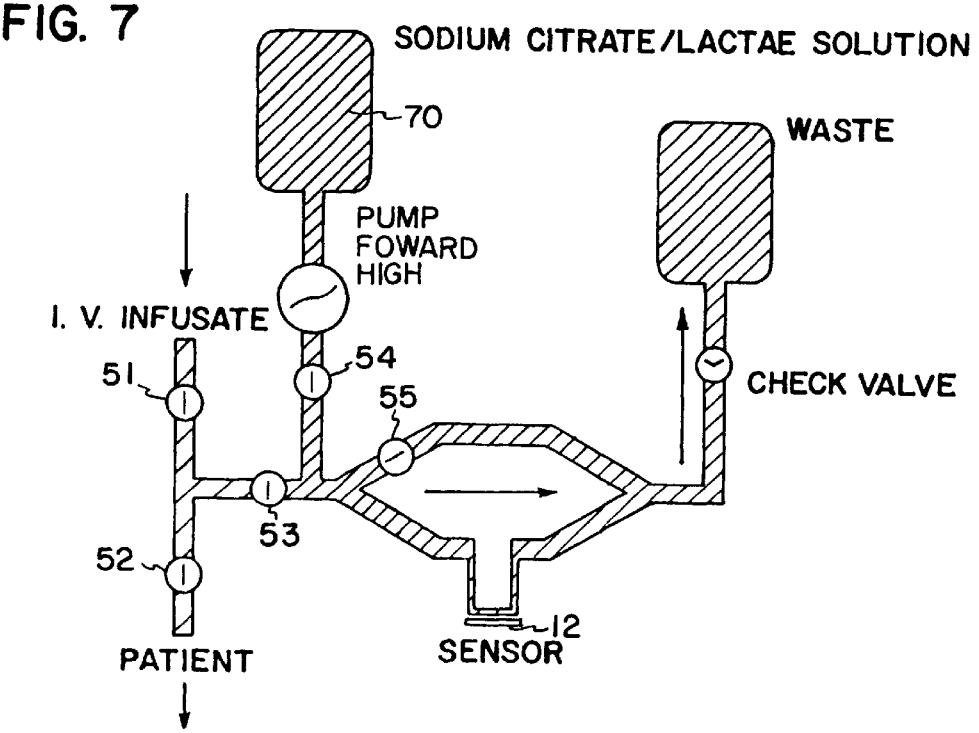

In FIG. 7, the assembly 100 is flushed with calibration/ anticoagulant solution. Valves 51 and 52 are open. Valves 54 and 55 are open. Valve 53 is closed. The pump 72 is running forward at high speed. This purges the system and coats the interior passages of assembly 100 with anticoagulant. The patient continues to be infused with saline.

Figure 8:
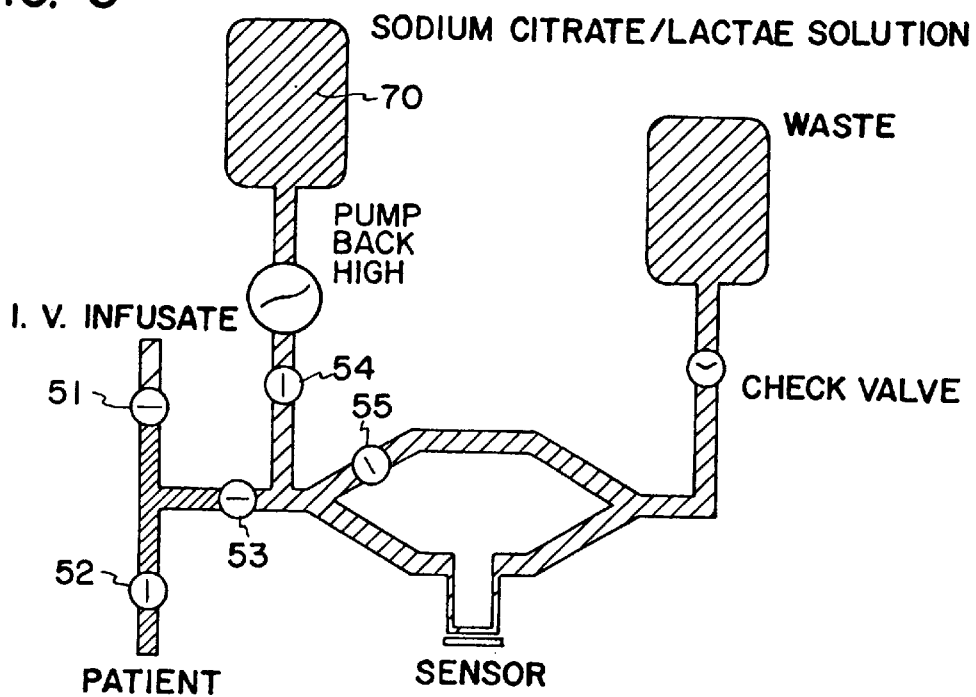

In FIG. 8, an undiluted sample of blood is drawn to a defined point beyond valve 54. Valve 51 is closed and valve 52 is open, thereby blocking the saline infusion. Valves 53 and 54 are open. Valve 55 is closed. The pump 72 is run in reverse direction at high speed. This draws a blood sample to a defined point beyond valve 54, and typically has an operation for approximately 5 to 10 seconds.

Figure 9:
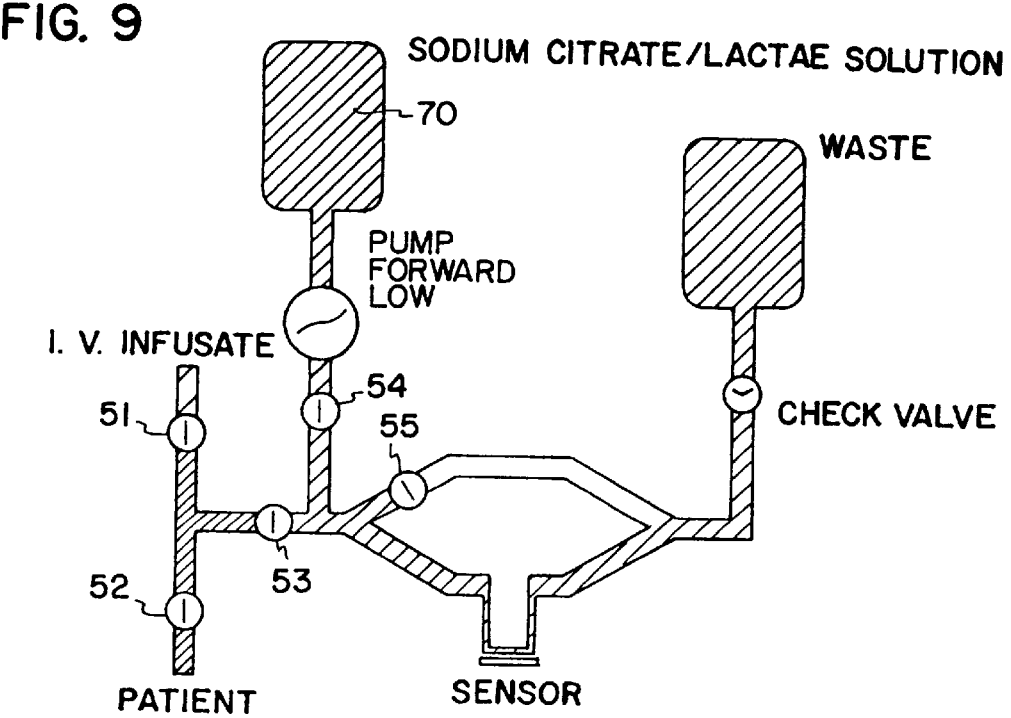

In FIG. 9, the patient infusion is resumed, and the blood sample is assayed. Valves 51 and 52 are open, allowing saline infusion. Valves 53 and 55 are closed. Valve 54 is open. The pump 72 is run forward at low speed. This directs all flow across the sensor 12. After a predetermined calibration and signal conditioning period, the sample is reported to a display.

Similar cycles of blood assay may be programmed by the medical technician to occur as frequently as once every five minutes.

The flow rate through the valve bodies may be varied from about 5 microliters to several milliliters per minute.

The bypass channel controlled by valve 55 allows high flow rates to be shunted around the sensor. The flow rate pass to the sensor is limited due to the size of the sensor. Excessive flows and turbulence may damage the sensor.

Figure 10:
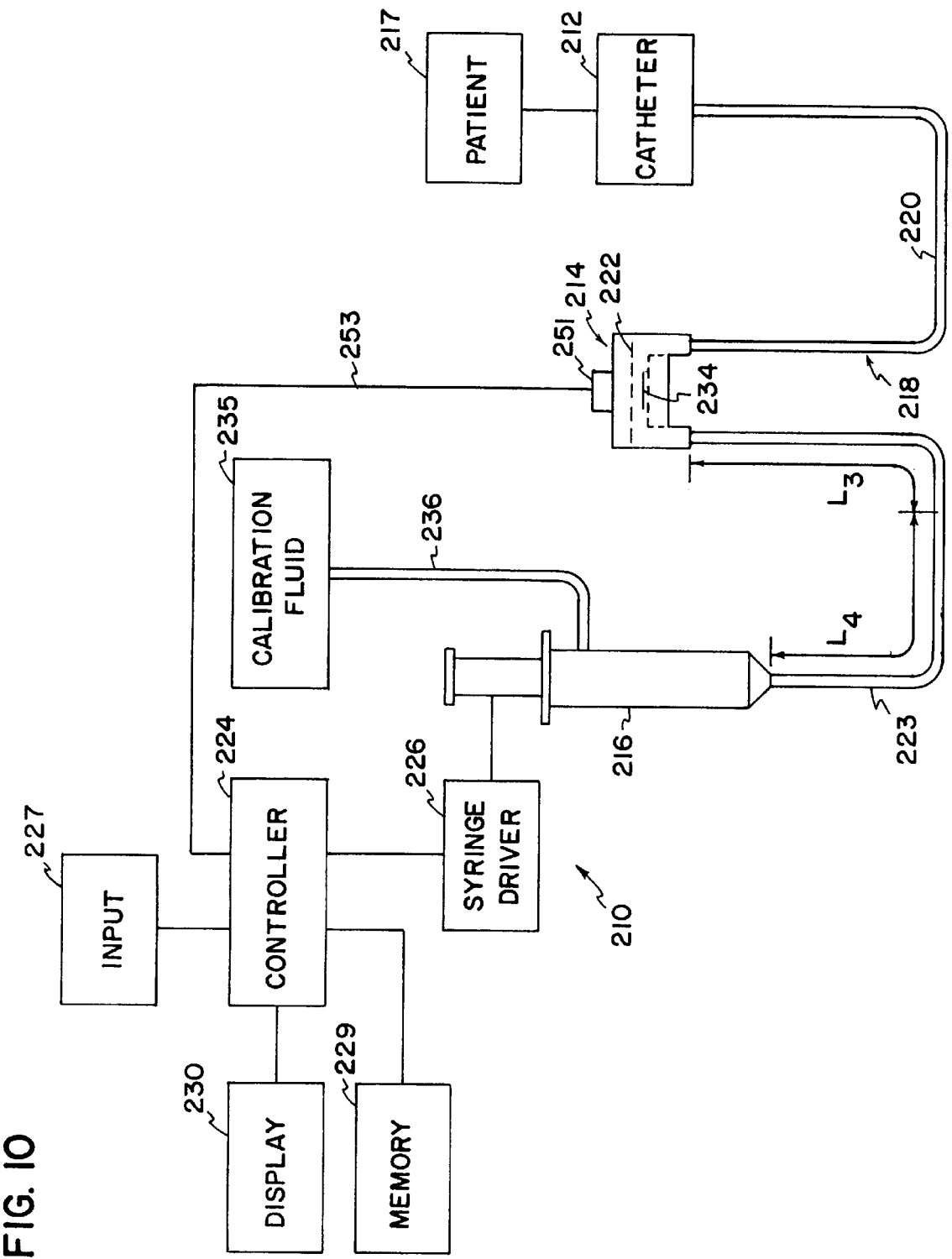
FIG. 10 is a schematic depiction of an embodiment of a sensor system or arrangement constructed in accordance with the principles of the present invention.

FIG. 10 illustrates a sensor system or arrangement 210 that is another embodiment of the present invention. One general aspect of the sensor arrangement 210 is to provide an ex vivo analyte sensor for the on-line measurement of bioanalytes such as lactate, glucose or other analytes. To promote manufacturing and operational efficiency, the system 210 preferably has a single uninterrupted flow path adapted to extend from a patient, past an analyte sensor, to a source of calibration fluid. The phrase "single uninterrupted flow path" is intended to mean that the system does not use valves or similar flow control devices to route flow between the patient and the source of calibration fluid.

The system is preferably a bi-directional system. The term "bidirectional" is intended to mean that flow is directed back and forth across the sensor through the single flow line. For example, flow can be directed in a first direction from the source of calibration fluid toward the patient. This allows the sensor to be calibrated and the entire flow path to be coated with anticoagulant. After calibration of the sensor and coating of the flow path with anticoagulant, flow in the system is preferably reversed to cause a fluid sample to flow from the patient across the sensor toward the source of calibration fluid. This allows an analyte level of the fluid sample to be measured by the sensor.

While in certain embodiments of the invention valves could be utilized, the bi-directional nature of the system eliminates the need for internal valves along the continuous flow path. The bi-directional nature of the system also reduces manufacturing costs. This is particularly significant in disposable systems.

To minimize patient discomfort, another general preferred aspect of the invention relates to using relatively low flow rates through the flow path. For example, flow rates less than 100 microliters per minute, or less than 50 microliters per minute, are preferred. Such low flow rates allow sample fluids to be drawn from low flow regions such as capillary beds thereby further reducing patient discomfort.

The general system described above provides a simple and relatively inexpensive system for monitoring analyte levels, such as lactate levels, in a patient. Because the system has a minimal number of parts, the system is ideally suited for disposability. The simplicity of the system also facilitates assembly and operation of the system.

Referring back to FIG. 10, the sensor arrangement 210 generally includes a catheter 212 for withdrawing a test fluid sample, a sensor module 214 for measuring an analyte such as lactate in the sample, and a syringe 216. A single uninterrupted flow path 218 extends between the syringe 216 and the catheter 212. The flow path 218 is formed by a first flow line 220 extending between the catheter 212 and the sensor module 214, a test chamber 222 formed through the sensor module 214, and a second flow line 223 extending between the sensor module 214 and the syringe 216. The sensor arrangement 210 also includes a control unit or controller 224 that interfaces with a syringe driver 226, an input unit 227 such as a keyboard, memory 229, an electrochemical sensor 234 within the sensor module 214, and a display unit 230 such as a monitor. A source of calibration fluid 235 preferably provides calibration fluid to the syringe 216 through a third flow line 236. The syringe 216 draws calibration fluid from the source of calibration fluid 235, and itself functions as a source of calibration fluid with respect to the second flow line 223.

It is preferred for the catheter 212 to be a relatively small diameter catheter capable of withdrawing blood samples from a capillary bed of a patient 217. Preferably, the catheter 212 is capable of withdrawing blood or other fluid samples at a rate less than 100 microliters per minute or less than 50 microliters per minute. Of course, conventional venous catheters and other types of catheters can also be utilized for withdrawing test fluids from a patient. Other techniques for withdrawing fluid samples from a patient in medical applications include intracranial pressure (ICP), microdialysis and iontophoresis.

The first, second and third flow lines 220, 223 and 236 are preferably formed by conventional medical tubing. In preferred embodiments, the flow lines 220 and 223 have inner diameters less than ⅛ inch or less than 0.1 inch, or about 0.010 inch. The relatively small diameters of the first and second flow lines 220 and 223 helps to inhibit mixing between fluid samples drawn through the catheter 212 and calibration fluid dispensed into the flow path 218 through the syringe 216. Mixing is inhibited because the dynamic frontier formed between the fluid sample and the calibration fluid has a small area so that contamination by diffusion is minimized. Additionally, mixing is also inhibited by maintaining laminar flow within the flow path 218.

By way of a non-limiting example, the source of calibration fluid can be a conventional intravenous (IV) bag that feeds calibration fluid to the syringe 216 via gravity through the third flow line 236. Of course, other devices, such as syringe pumps, pneumatic pumps and peristaltic pumps, can also be used. A preferred calibration fluid to be supplied to the syringe 216 includes a predetermined concentration of a calibrant such as lactate for lactate sensors, or glucose for glucose sensors. The calibration fluid can include a variety of other components in addition to a calibrant. For example, an anticoagulant such as sodium citrate can be used. A preferred calibration fluid comprises a solution of sodium citrate, saline and lactate. Of course, lactate is only used as a calibrant if a lactate sensor is being used in the system. Other types of calibrants that may be used in the system include glucose, potassium, sodium, calcium and ringers lactate.

It will be appreciated that the control unit 224 can include any type of controller such as a micro-controller, a mechanical controller, an electrical controller, a hardware driven controller, a firmware driven controller or a software driven controller. Similarly, the syringe driver 226, display unit 230, and the input unit 227 can comprise off the shelf components. For example, a suitable device incorporating a controller, a display unit, an input unit, and a syringe driver is sold by Alaris Corporation of San Diego, Calif. under the name Ivac, or by Medex Corporation of Hilliard, Ohio under the name MedFusion.

The electrochemical sensor 234 of the sensor arrangement 210 is preferably a wired enzyme sensor for detecting or measuring bioanalytes. Illustrative wired enzyme sensors are described in U.S. Pat. Nos. 5,264,105; 5,356,786; 5,262,035; and 5,320,725, herein incorporated by reference.

Figure 11:
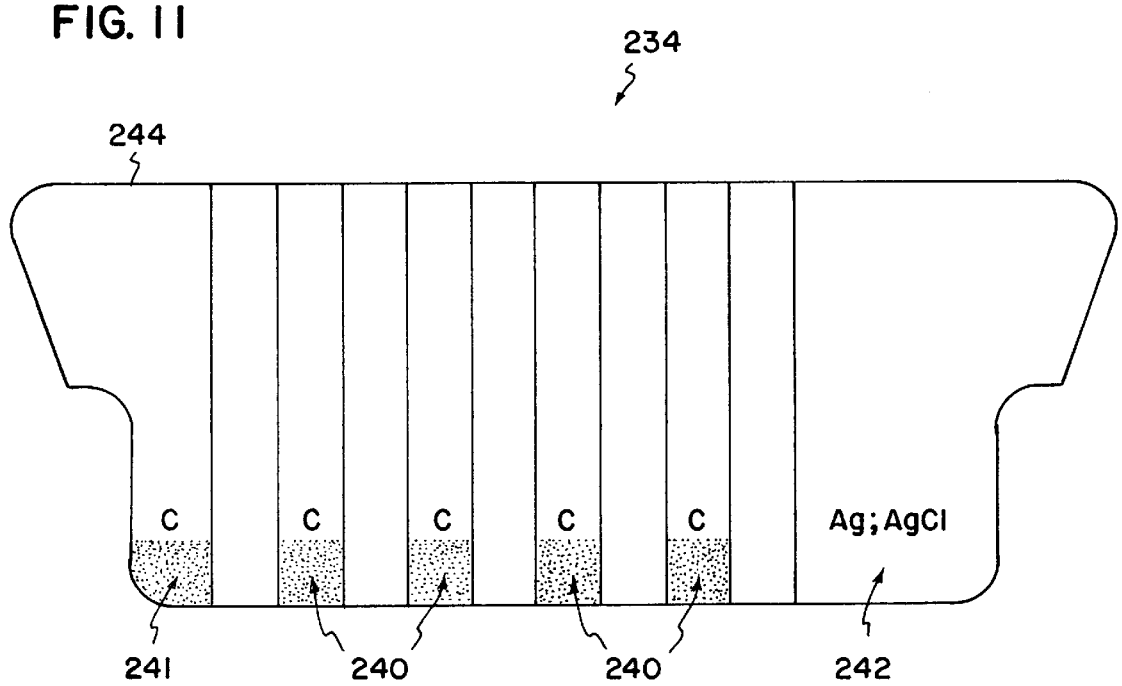
FIG. 11 is a plan view of an embodiment of a sensor suitable for use with the system of FIG. 10.

FIG. 11 is a plan view of one embodiment of the electrochemical sensor 234 that can be incorporated within the sensor module 214. The sensor 234 includes four spaced-apart working electrodes 240, a counter electrode 241 and a reference electrode 242. The working, counter and reference electrodes 240, 241 and 242 are formed as separate conductive lines or traces on a conventional flexible circuit board 244. At least portions of the working, counter and reference electrodes 240, 241 and 242 are positioned along the test chamber 222 of the sensor module 214.

The working electrodes 240 are electrodes at which an analyte such as lactate or glucose is electrooxidized or electroreduced. Current is passed between the working electrodes 240 and the counter electrode 241. The potential of the working electrodes 240 is monitored relative to the reference electrode 242. Since essentially no current is passed through the reference electrode 242, its potential will remain constant and equal to its open-circuit value. This system is called a three-electrode system.

If the current is small, a two-electrode system can be used. That is, the counter electrode 241 can be used as a working electrode too, and the reference electrode 242 will also act a counter electrode. Since the current is small, the passage of the low current through the reference electrode 242 will not effect the potential of the reference electrode 242.

The working, counter and reference electrodes 240, 241 and 242 arc positioned within the test chamber 222. The chamber 222 is configured so that when a sample is provided in the chamber 222, the sample is in fluid contact with both the working, counter and reference electrodes 240, 241 and 242. This allows electrical current to flow between the electrodes 240, 241 and 242 to effect the electolysis (electrooxidation or electroreduction) of the analyte.

The working/counter electrodes 240 and 241 may be formed by any conductive material. Exemplary conductive materials include carbon, gold, platinum, graphite, palldium and tin oxide. The working electrodes 240 preferably have test surfaces that are covered with a sensing layer. The sensing layer preferably includes a redox compound or mediator. The term redox compound is used herein to mean a compound that can be oxidized and reduced. Exemplary redox compounds include transition metal complexes with organic ligands. Preferred redox compounds/mediators are osmium transition metal complexes with one or more ligands having a nitrogen containing heterocyde such as 2,2'-bipyridine. The sensing layer can also include a redox enzyme. A redox enzyme is an enzyme that catalyzes an oxidation or reduction of an analyte. For example, a glucose oxidase or glucose dehydrogenase can be used when the analyte is glucose. Also, a lactate oxidase or lactate dehydrogenase fills this role when the analyte is lactate. In systems such as the one being described, these enzymes catalyze the electrolysis of an analyte by transferring electrons between the analyte and the electrode via the redox compound.

For the sensor 234 depicted in FIG. 11, only one working electrode is required to monitor or detect a particular analyte. Multiple working electrodes are provided to allow different analytes to be monitored.

The reference electrode 242 can be constructed in a manner similar to the working/counter electrodes 240 and 241. Suitable materials for the reference electrode 242 include Ag/AgCl printed on a non-conducting base material or silver chloride on a silver metal base.

In use of the electrochemical sensor 234, a previously determined potential is applied across the working and reference electrodes 240 and 242. When the potential is applied and a sample fluid containing the desired analyte is in the test chamber 222, an electrical current will flow between the working electrode 240, counter electrode 241 and reference electrode 242. The current is a result of the electrolysis of the analyte in the sample fluid. This electrochemical reaction occurs via the redox compound and the optional redox enzyme. By measuring the current flow generated at a given potential, the concentration of a given analyte in a test sample can be determined.

Those skilled in the art will recognize that current measurements can be obtained by a variety of techniques including, among other things, coulometric, potentiometric, amperometric, voltammetric, and other electrochemical techniques.

The measurements obtained by typical non-coulometric techniques are generally temperature dependent. Consequently, temperature data generated by a temperature probe is used to generate reliable analyte data for such techniques. In certain embodiments of the present invention, a temperature probe can be formed as a line on the printed circuit board 244. Alternatively, temperature probes can be located elsewhere within the chamber 222, outside the test chamber 222, or at alternative locations along the flow path 218. The temperature probes preferably interface with the control unit 224.

Figure 12:
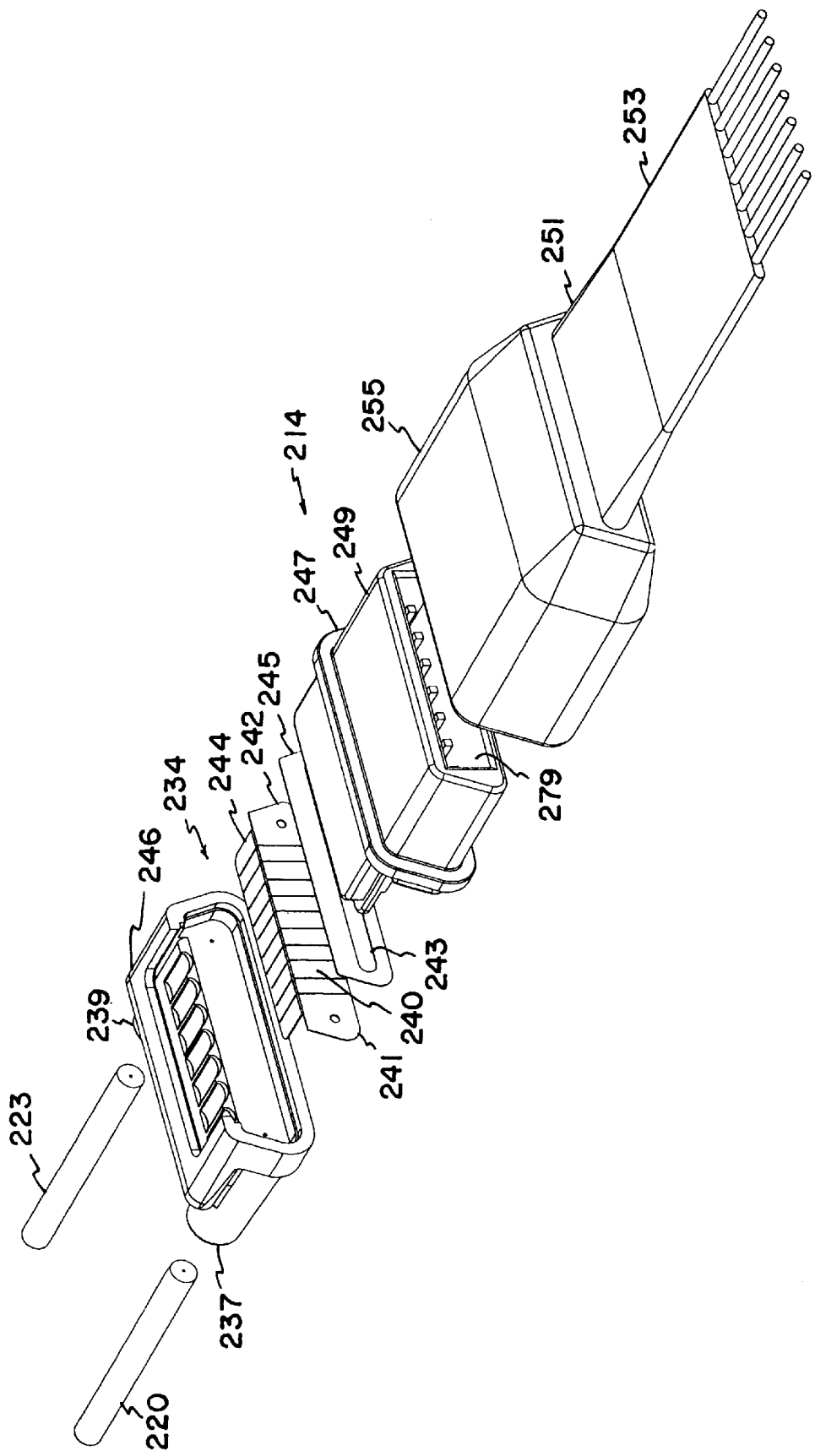
FIG. 12 is an exploded perspective view of an embodiment of a sensor module constructed in accordance with the principles of the present invention.

FIG. 12 is an exploded perspective view of the sensor module 214. As shown in FIG. 12, the sensor module includes a terminal housing 247 adapted to be connected to a sensor housing 246. The flexible circuit board 244 and a layer of pressure sensitive adhesive 245 are positioned between the terminal and sensor housings 247 and 246. The pressure sensitive adhesive 245 defines an elongated slot 243 that extends across a width of the sensor module 214. The sensor housing 246 includes a first port 237 adapted for connection to the first flow line 220, and a second port 239 adapted for connection to the second flow line 223.

Figure 14A:
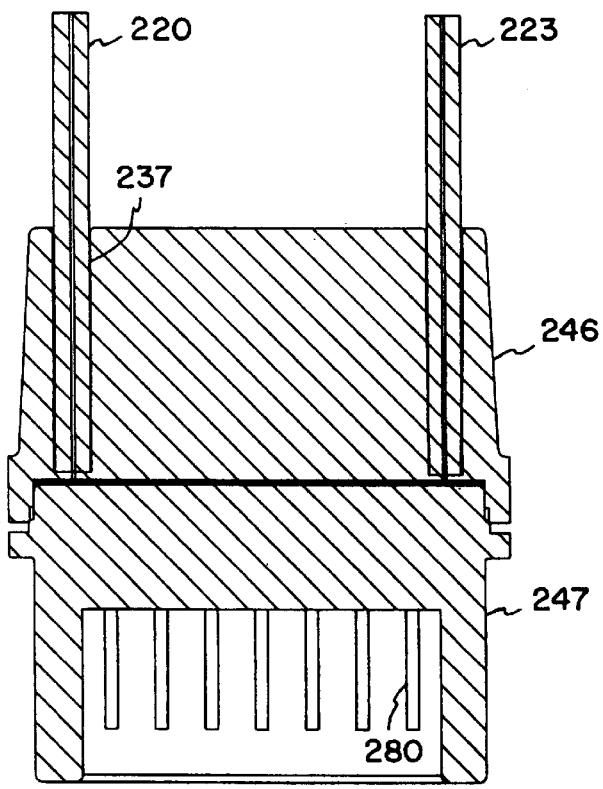
FIG. 14A is a cross-sectional view cut lengthwise through the sensor module of FIG. 13.

Referring still to FIG. 12, the terminal housing 247 of the module 214 includes an output end 249 including a connector port 279 having a plurality of connector pins 280 (shown in FIG. 14A). Six of the connector pins 280 are in electrical connection with corresponding electrodes 240, 241 and 242 of the flexible circuit board 244. A seventh pin 280 is a redundant/expansion pin for use in future development. In use, an electrical connector 251 is inserted within the connector port 279 and connected to the pins 280. An flexible electrical cable 253 provides a connection between the connector 251 and the controller 224. The cable 253 allows the controller 224 to apply a potential across the working and reference electrodes 240 and 242, and monitor the resulting current. The connector 251 includes a resilient skirt 255 that forms a fluid tight seal around the output end 249 of the terminal housing 247.

Figure 13:
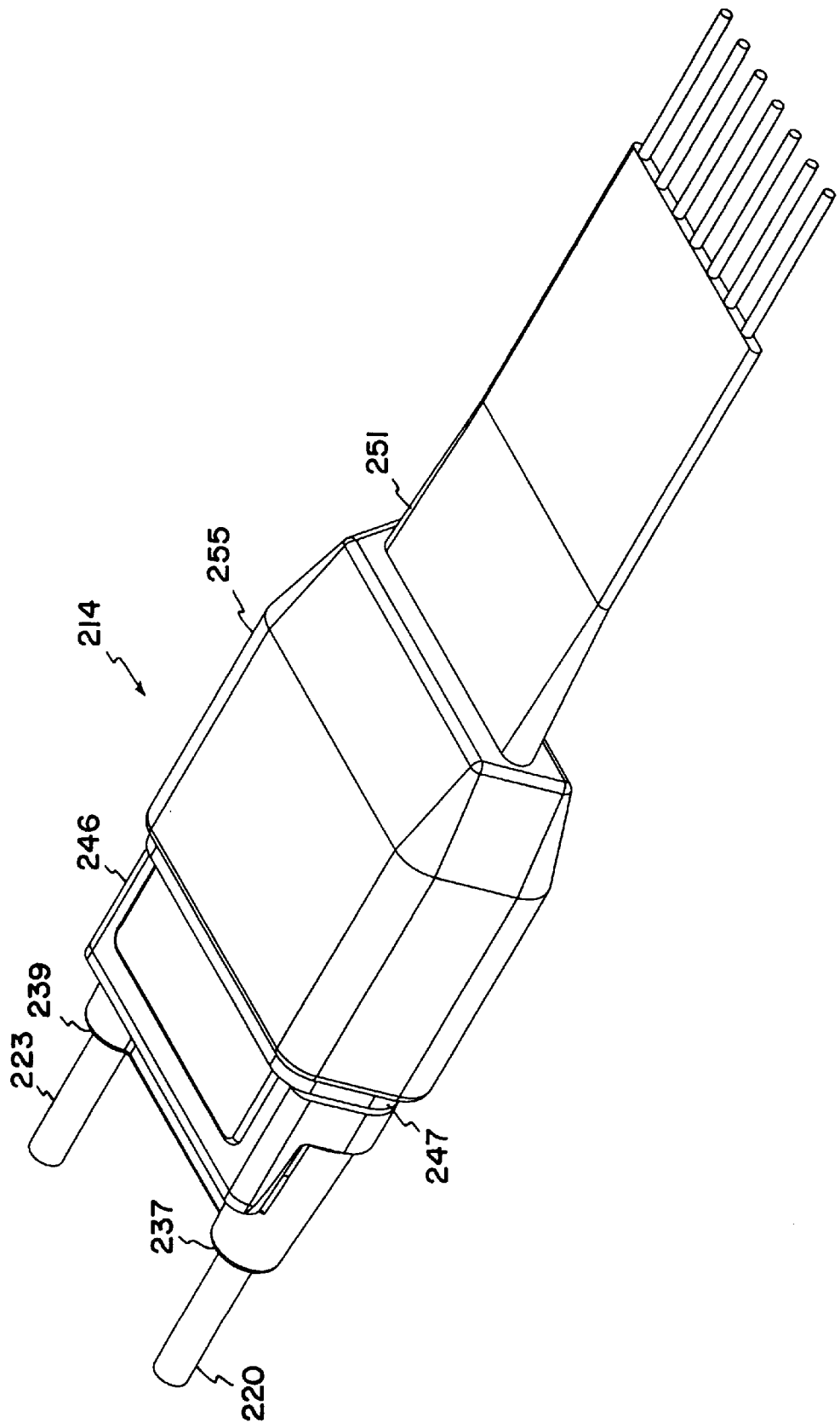
FIG. 13 is a perspective view of the sensor module of FIG. 12 as assembled.

FIG. 13 shows the sensor module 214 assembled. As assembled, the sensor and terminal housings 246 and 247 mate together, and the flexible circuit board 244 and the adhesive layer 245 are captured between the housings 246 and 247. Also, the first and second flow lines 220 and 223 are inserted within the first and second ports 237 and 239, and the resilient skirt 255 of the connector 251 is inserted over the output end 249 of the terminal housing 247.

Figure 14B:
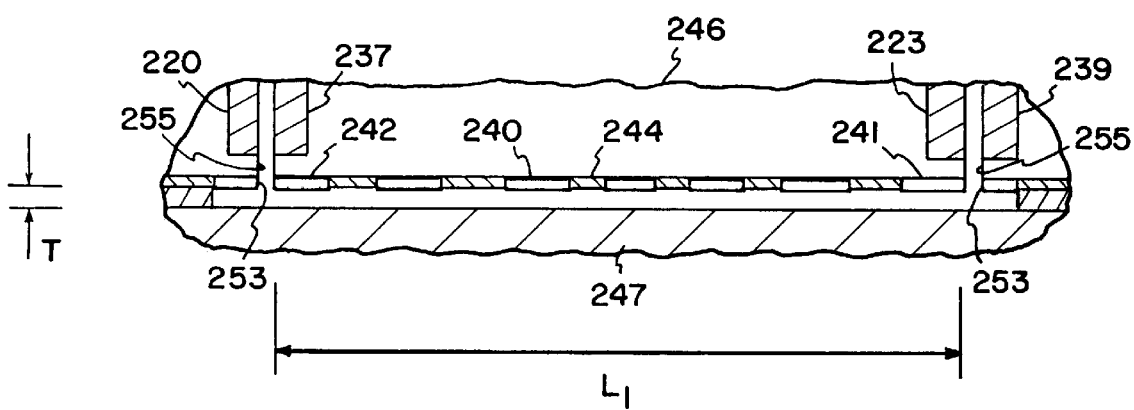
FIG. 14B is an enlarged view of a portion of FIG. 14A.

Referring to FIGS. 14A and 14B, the test chamber or cell 222 of the sensor module 214 extends transversely between the first and second ports 237 and 239 of the sensor housing 246. At least portions of the working/counter electrodes 240, 241 and the reference electrode 242 of the electrochemical sensor 234 are positioned within the test chamber 222. First holes 253 defined by the flexible circuit board 244 and second holes 255 defined by the sensor housing 246 provide fluid communication between the test cell 222 and the first and second flow lines 220 and 223.

The test cell 222 is formed between the terminal and sensor housings 246 and 247 of the sensor module 214. Void space for the test cell 222 is provided by the elongated slot 243 formed in the layer of pressure sensitive adhesive 245. The adhesive 245, which is compressed between the housings 246 and 247, also provides a fluid tight seal around the test cell 222. Other types of adhesives, such as ultraviolet curable adhesives, can be used to further seal the sensor module 214.

It is preferred for a thin sheet of test fluid to flow through the test cell 222. Consequently, it is preferred for the test cell 222 to have a thickness T less than 0.1 inch, or less than 0.01 inch, or about 0.005 inch. A preferred length $L_1$ of the test cell 222 is about 0.5 inch. A preferred width of the test cell 222 (in a direction perpendicular to the thickness T and the length L) is in a range of 0.05 to 0.07 inch.

To inhibit mixing within the flow path 218, it is preferred to maintain laminar flow throughout the flow path 218. To facilitate maintaining laminar flow in the transition between the first and second flow lines 220 and 223 and the test cell 222, it is preferred for the test cell 222 to have approximately the same cross sectional area as each of the first and second flow lines 220 and 223. The cross sectional area of the test cell 222 is preferably taken along a plane generally transversely aligned with respect to a direction of flow through the test cell 222.

Figure 15:
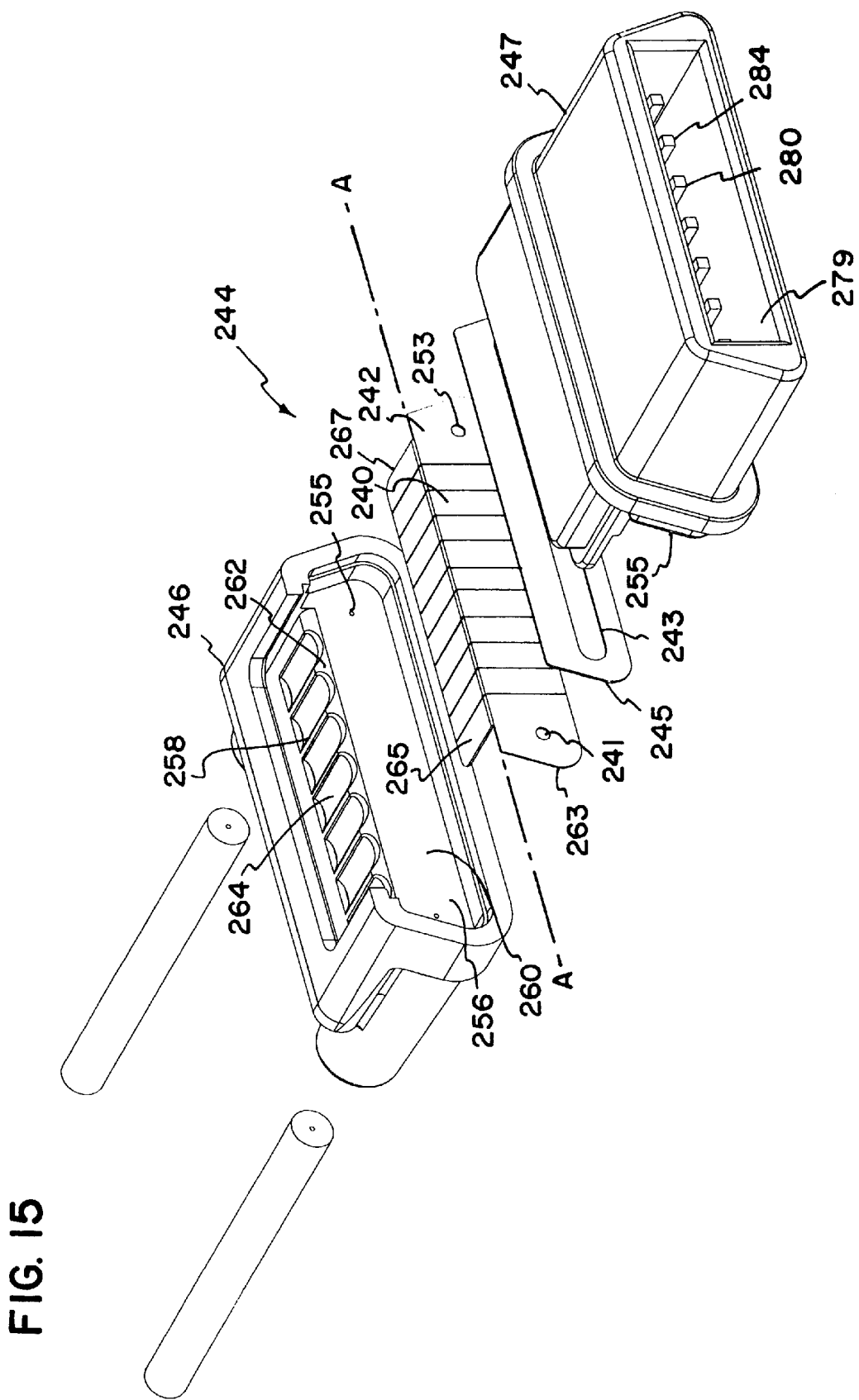
FIG. 15 is another exploded perspective view of the sensor module of FIG. 12.

Referring now to FIGS. 15, the terminal housing 247 includes an input end portion 255 that mates or fits within a corresponding recessed portion 256 defined by the sensor housing 246. The recessed portion 256 of the sensor housing 246 is sized and shaped for holding the flexible circuit board 244 of the electrochemical sensor 234. The recessed portion 256 of the sensor housing 246 is defined by first and second transversely aligned walls 258 and 260. The first and second walls 258 and 260 intersect at a fold edge 262. The second wall 260 is generally planer while the first wall 258 defines a plurality of generally parallel recesses or depressions 264. The second holes 255 of the sensor housing 246 open through the second wall 260. As previously described, the second holes 255 provide fluid communication between the test chamber 222 and the first and second flow lines 220 and 223.

Figure 16:
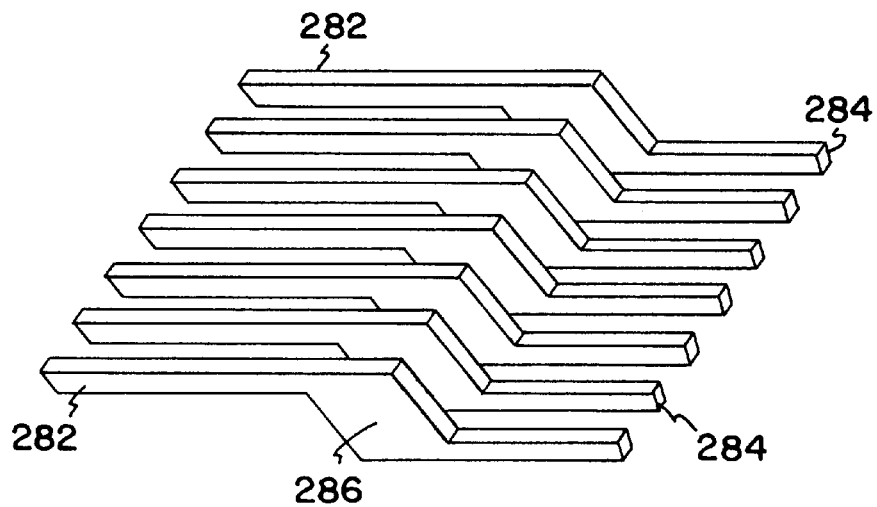
FIG. 16 is a perspective view of connector pins used in the sensor module of FIG. 12.

Referring still to FIG. 15, the connector pins 280 that are housed within the terminal housing 247 include output end portions 284 positioned within the connector port 279. As shown in FIG. 16, the output end portions 284 are connected to input end portions 282 by intermediately located transverse portions 286. The input and output end portions 282 and 284 are preferably generally parallel with respect to one another.

The flexible circuit board 244 is adapted to be mounted within the recessed portion 256 of the sensor housing 246. A lower portion 263 of the flexible circuit board 244, including the electrodes 240, 241 and 242, is adapted to align flat against the second wall 260. When the sensor module 214 is assembled, the flexible circuit board 244 is folded along fold line A—A that corresponds to fold edge 262, such that an upper portion 267 of the flexible circuit board 244 lies flat against the first wall 258 of the sensor housing 246. The upper portion 264 of the flexible circuit board 244 includes leads 265 that are connected to the working and counter electrodes 240 and 242. When the upper portion 264 is positioned in the folded orientation and inserted within the recessed portion 256, each lead 265 is positioned directly above a corresponding depression 264 defined by the first wall 258.

Figure 17:
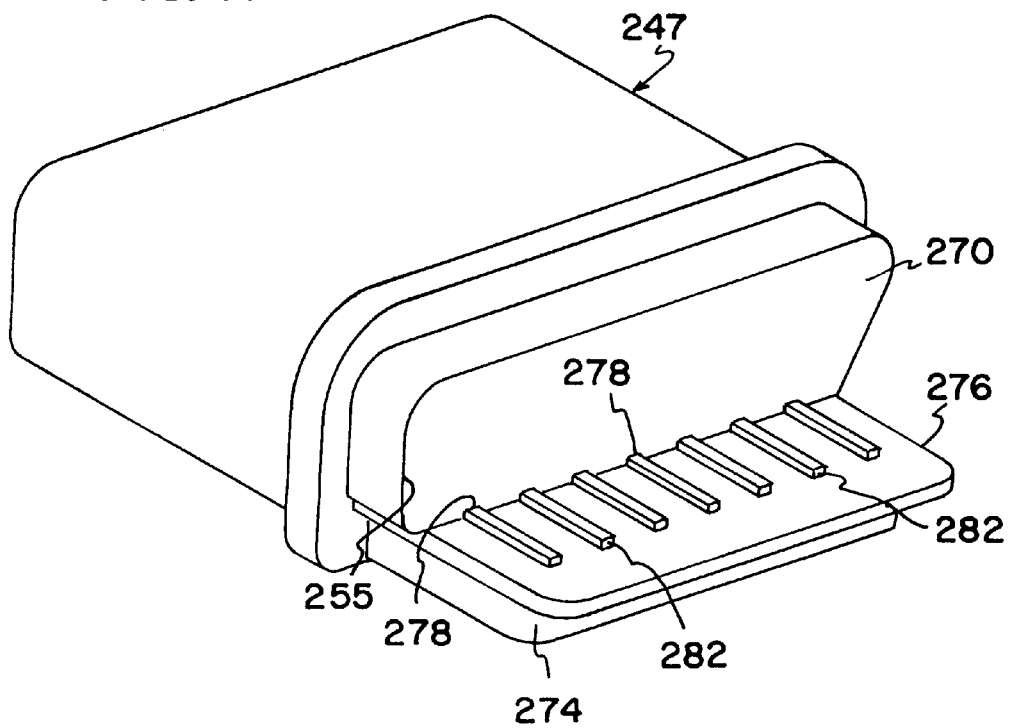
FIG. 17 is a perspective view of an input end of the terminal housing of the sensor module of FIG. 12.

Referring now to FIG. 17, the input end 255 of the terminal housing 247 includes a wall 270 adapted to face the lower portion 263 of the flexible circuit board 244 when the sensor module 214 is assembled. The input end 255 of the terminal housing 247 further includes an axial flange 274 that is generally transversely aligned with respect to the wall 270. The axial flange 274 includes a surface 276 adapted to face the first wall 258 of the sensor housing 246 when the sensor module 214 is assembled. The wall 270 of the terminal housing 247 also includes a plurality of spaced apart openings 278 positioned adjacent a region where the axial flange 274 intersects with the wall 270. As shown in FIG. 17, the input end portions 282 of the connector pins 280 extend through the openings 278.

As assembled, the input end portion 255 of the terminal housing 247 mates within the recessed portion 256 of the sensor housing 246. The input end portions 282 of the connector pins 280 are inserted through the holes 278 of the terminal housing 247 and extend along the surface 276 of the axial flange 274 (as shown in FIG. 17). The input end portions 282 of the connector pins 280 engage the leads 265 formed on the upper portion 264 of the flexible circuit board 244. The input end portions 282 and the flexible circuit board 244 are compressed between the axial flange 274 of the terminal housing 247 and the first wall 258 of the sensor housing 246. Such compression causes the flexible circuit board 244 to deform within the parallel depressions 264 defined along the top surface of the first wall 258. The output end portions 284 and the transverse portions 286 of the connector pins 280 are positioned within the connector port 279 defined by the output end 249 of the terminal housing 247.

While a variety of fluid control/sampling/pumping devices could be used to control fluid flow through the flow path 218 of the sensor arrangement 210, a preferred pumping device has a piston-like structure for conveying fluid. One exemplary device is the modified syringe 216 shown schematically in FIGS. 18A and 18B. The syringe 216 includes a syringe housing 290 that defines a piston chamber 292. The syringe housing 292 also defines first and second ports 294 and 296 that provide access to the piston chamber 292. The first port 294 is axially spaced a distance D from the second port 296. The first port 294 is preferably connected to the third flow line 236 that provides calibration fluid to the syringe 216, while the second port 296 is preferably to the second flow line 223.

The syringe housing 290 includes an open end portion 298 positioned opposite from a closed end portion 300. A side wall 302 extends between the open and closed end portions 298 and 300. The second port 296 extends through the closed end portion 300 or base, while the first port 294 extends through the side wall 302.

The piston chamber 292 is aligned along a longitudinal axis A—A. The first port 294 extends in a radial direction relative to the longitudinal axis A—A, while the second port 296 extends in an axial direction relative to the longitudinal axis A—A.

The first port 294 is shown located in close proximity to the upper edge of the side wall 302. However, it will be appreciated that the first port 294 can be located at various locations along the side wall 302. Additionally, as shown in FIGS. 18A and 18B, an uninterrupted flow path is provided between the first port 294 and the source of calibration fluid. However, it will be appreciated that in certain embodiments, it may be desirable to place a check valve at the first port 294 or somewhere along the third flow line 236 to inhibit back flow through the third flow line 236.

The piston 228 of the syringe 216 is mounted for reciprocal movement within the piston chamber 292 of the syringe housing 290. Preferably, the piston 228 is reciprocated in a controlled manner through the syringe driver 226 that is controlled by the control unit 224. The piston 228 includes an elongated head 304 having a length $L_2$ that is preferably at least as long as a maximum stroke length of the piston 228. The maximum stroke length of the piston is measured from the top of the first port 294 to the farthest point the piston penetrates within the piston chamber 292.

As shown in FIGS. 18A and 18B, the piston 228 is moveable between a first position (shown in FIG. 18A) in which the first port 294 is open and calibration fluid can enter the piston chamber 292, and a second position (shown in FIG. 18B) in which the piston head 304 blocks the first port 294 such that calibration fluid is inhibited from entering the piston chamber 292. At least a portion of the piston head 304 is preferably made of a generally resilient or elastomeric material capable of forming a generally fluid tight seal between the piston head 304 and the side wall 302 of the syringe housing 290.

In use, the piston 228 is moved to the first position (FIG. 18A) such that the calibration fluid flows from the source of calibration fluid 235 by gravity into the piston chamber 292. As the calibration fluid flows through the first port 294 into the piston chamber 292, calibration fluid is also forced via gravity out the piston chamber 292 through the second port 296. Consequently, flow from the source of calibration fluid 235 causes calibration fluid to flow from the syringe 216 through the flow path 218 toward the catheter 212. A preferred gravity flow rate from the syringe 216 is in the range of 50–100 microliters/minute or less than 50 microliters/minute.

To impart a controlled flow of fluid within the flow path 218, the piston 228 is driven toward the second position (FIG. 18B) at a controlled rate thereby causing calibration fluid to be forced from the piston chamber 292 into the second flow line 223. Once a lower edge of the piston head 304 moves below the first port 294, the first port 294 is effectively blocked such that calibration fluid is inhibited from entering the piston chamber 292 through the first port 294 while the piston forces calibration fluid out the second port 296.

After a desired volume of calibration fluid has been forced through the second port 296 by the piston 226, the piston 228 can reverse direction and draw a predetermined flow rate of calibration fluid from the second flow line 223 through the second port 296 into the piston chamber 292. A fluid sample is also drawn through the catheter 212 and toward the sensor module 214. The piston 226 moves back until it reaches the first position depicted in FIG. 18A. Upon reaching the first position of FIG. 18A, the before mentioned cycle can be repeated.

In use of the sensor arrangement 210, the flow path 218 is initially purged of air. With the piston 228 of the syringe 216 in the first position of FIG. 18A, calibration fluid (preferably containing a calibrant and an anticoagulant) from the source of calibration fluid 235 flows into the piston chamber 292 through the first port 294, and flows down through the piston chamber 292 into the flow path 218. In this manner, the calibration fluid is dispensed through the flow path 218 so that the interior surfaces of the fluid system are coated with a layer fresh anticoagulant. Small amounts of the calibration fluid may be infused into the patient 217 through the catheter 212.

Once the flow path 218 is filled with calibration fluid, the control unit 224 commands the syringe driver 226 to push the piston 228 into the piston chamber 292 at a predetermined rate so as to cause the calibration fluid to flow through the flow line 218 toward the patient 217 at a predetermined flow rate, such as between 5–100 microliters per minute, or less than 50 microliters per minute.

The calibration fluid flows along the flow path 218 toward the patient at a predetermined rate for a predetermined time sufficient to both allow the electrochemical sensor 234 to be calibrated and to coat the interior surfaces of the fluid system with fresh anticoagulant. A single stroke length of the piston 228 preferably displaces a volume of calibration fluid that is equal to the internal volume of the first flow line 220 plus the internal volume of the test chamber 222 plus the internal volume of a length $L_3$ of the second flow line 223.

Once the predetermined volume of calibration fluid has been dispensed from the syringe 216, the control unit 224 commands the syringe driver 226 to pull back on the piston 228 causing the syringe 216 to aspirate a fluid (i.e. blood) sample from the patient 217. The fluid sample is drawn through the catheter 212 into the first flow line 220 preferably at a rate less than 50 microliters per minute. From the first flow line 220, the fluid sample flows through the test chamber 222 and into the second flow line 223. The test fluid is drawn into the second flow line 223 until the sample fluid reaches the end of the length $L_3$ of the second flow line 223. When the sample fluid reaches the end of the length $L_3$ of the second flow line 223, the piston 228 concurrently preferably reaches the first position of FIG. 18A.

When the piston 226 reaches the first position of FIG. 18A, the syringe driver 226 stops the piston 228 and fresh calibration fluid begins to flow into the syringe 290 through the first port 294. As the fresh calibration fluid enters the syringe 226, sample fluid is gradually flushed from the flow line 218 back into the patient. Once the flow path 218 has been re-filled with calibration fluid, the cycle can be repeated.

In selecting the length $L_3$ and its corresponding internal volume, a number of factors should be taken into consideration. First, a sufficient length $L_4$ of buffer region should exist for inhibiting calibration fluid within the piston chamber 292 from being contaminated. Also, the volume associated with the length $L_3$ should be sufficiently large to allow the electrochemical sensor 234 to take an accurate reading of the test sample. In other words, the electrochemical sensor 234 should be exposed to the test sample for a predetermined amount of time in order to take an accurate reading. Consequently, depending upon the rate of flow through the flow path 218, the length of tubing $L_3$ should provide a large enough volume to accommodate the fluid sample that should flow past the sensor 234 during testing. For example, if the electrochemical sensor 234 should be exposed to a test sample for one minute in order to provide an accurate reading, and the flow rate through the system is 50 microliters per minute, the length $L_3$ of tubing should provide a volume of at least 50 microliters.

For certain applications, the control unit 224 can be programmed to cause the sensor arrangement 210 to take fluid samples at predetermined time intervals. For example, samples can be taken every hour, or every fifteen minutes, or every five minutes. During the time periods between sampling, the entire flow path 218, including the sensor 234, is preferably bathed in calibration fluid.

The sensor arrangement 210 is particularly suited for use as a disposable ex vivo lactate monitor. When used as a lactate monitor, the sensor arrangement 210 can automatically, via the controller 224, sample lactate readings at predetermined intervals such as every hour, every fifteen minutes, or every five minutes. Current lactate readings can be displayed on the display unit 230. Furthermore, trends such as increases in lactate concentration, decreases in lactate concentration, and rates of lactate concentration change can be stored in memory 229 associated with the control unit 224. Such information can be used to provide a physician with a data such as a lactate history line or an average lactate reading for a particular patient on a given day.

It will be appreciated that information such as sampling intervals, sampling volumes and desired flow rates through the system can be provided to the controller via the input device. Also, information stored in memory can be accessed via the input device. Furthermore, flow within the system can be monitored and controlled by techniques such as monitoring the volume displaced by the syringe, timing systems, or through the use of sensors positioned at various locations along the flow path 218.

FIG. 19 is an exploded perspective view of a preferred pumping device 320 constructed in accordance with the principles of the present invention. The pumping device 320 is adapted for use in sensor systems such as the arrangement 210 shown in FIG. 10.

The pumping device 320 includes a housing 322 including an upper pump housing 324, a lower pump housing 326, and a manifold 328 positioned between the upper and lower pump housing 324 and 326. An axial bore or piston chamber 330 extends axially through the housing 322. The lower pump housing 326 includes a base 332 defining an end port 334 in fluid communication with the piston chamber 330. The manifold 328 defines a side port 336 that is also in fluid communication with the piston chamber 330. As shown in FIG. 19, an elongated, resilient lower seal 338 is positioned between the manifold 328 and the lower pump housing 326. Similarly, an elongated, resilient upper seal 340 is positioned between the upper pump housing 324 and the manifold 328. The pumping device 320 also includes an elongated, cylindrical piston member 342 adapted to be reciprocally mounted within the piston chamber 330, and a drive knob 344 adapted to be connected to an end of the piston member 342. The piston member 342 can be made of a material such as stainless steel.

FIG. 20 shows the pumping device 320 as assembled. As shown in FIG. 20, the upper and lower pump housings 324 and 326 matingly engage the manifold 328. The upper seal 340 is inserted within the upper pump housing 324 and is also inserted over a first neck portion 346 (shown in FIG. 19) of the manifold 328. Similarly, the lower seal 338 is inserted within the lower pump housing 326 and is also inserted over a second neck portion 348 (shown in FIG. 19) of the manifold 328. The piston member 342 is reciprocally mounted within the piston chamber 330 of the housing 322, and extends through the upper and lower seals 340 and 338. The lower seal 338 forms a generally fluid tight seal around the piston member 342 at a location below the manifold 328, while the upper seal 340 forms a generally fluid tight seal around the piston member 342 at a location above the manifold 328. The knob 344 is secured to the end of the piston member 342.

In use, the pumping device 320 operates in a manner similar to the modified syringe 216 shown in FIGS. 18A and 18B. For example, the side port 336 can be connected to a source of fluid such as a calibration fluid, while the end port 334 can be connected to a flow path in fluid communication with a sample fluid. By pushing the piston member 342 into the piston chamber 330, the fluid within the piston chamber 330 is forced out of the end port 334. As long as the end of the piston member 342 extends beyond the side port 336, the piston member 342 itself prevents fluid from being forced out of the piston chamber 330 through the side port 336. When the piston member 342 is pulled in a direction out of the piston chamber 330, fluid is drawn into the piston chamber 330 through the end port 334. When the end of piston member 342 moves past the side port 336, fluid is allowed to enter the piston chamber 330 through the side port.

With regard to the foregoing description, it is to be understood that changes may be made in detail, especially in matters of construction materials employed and the shape, size and arrangement of the parts without departing from the scope of the present invention. For example, the various aspects of the present invention are not limited to medical environments and are also applicable to other environments such as the measurement of analytes in industrial, manufacturing or agricultural settings. It is intended that the specification and depicted aspects be considered exemplary only, with a true scope and spirit of the invention being indicated by the broad meaning of the following claims.

We claim:

1. An on-line lactate sensor arrangement comprising:
   a lactate sensor;
   a first fluid flow line for drawing a fluid sample from a patient and conveying the fluid sample to the lactate sensor;
   a source of sensor calibration fluid;
   a second fluid flow line providing fluid communication between the source of sensor calibration fluid and the lactate sensor; and a source of pressure for pushing sensor calibration fluid from the source of sensor calibration fluid toward the lactate sensor, and a source of vacuum for drawing the fluid sample from the patient toward the lactate sensor, wherein both the source of pressure and the source of vacuum are provided by a syringe.

2. The sensor arrangement of claim 1, wherein the lactate sensor is an electrochemical sensor.

3. The sensor arrangement of claim 2, wherein the lactate sensor includes a flexible circuit board.

4. The sensor arrangement of claim 1, wherein the lactate sensor includes an electrode covered with a sensing layer including a redox compound and a redox enzyme.

5. The sensor arrangement of claim 4, wherein the redox enzyme includes lactate oxidase.

6. The sensor arrangement of claim 4, wherein the redox enzyme includes lactate dehydrogenase.

7. The sensor arrangement of claim 1, wherein the first and second fluid flow lines form at least portions of a valveless flow path extending between the patient and the source of sensor calibration fluid.

8. The sensor arrangement of claim 1, further comprising a sensor housing defining a test chamber in fluid communication with the first and second flow lines, at least a portion of the sensor being positioned within the test chamber.

9. The sensor arrangement of claim 1, wherein the test chamber has a depth less than 0.1 inch.

10. The sensor arrangement of claim 1, wherein the test chamber has a width in the range of 0.05 to 0.07 inch.

11. The sensor arrangement of claim 1, wherein the first flow line has an inner diameter less than 0.1 inch.

12. The sensor arrangement of claim 1, wherein the syringe defines a piston chamber and includes a piston mounted for reciprocal movement within the chamber, the chamber being formed by a side wall defining a first port and a base defining a second port, the first port providing fluid communication between the chamber and the source of sensor calibration fluid, and the second port providing fluid communication between the chamber and the second fluid flow line.

13. The sensor arrangement of claim 12, wherein the first port is positioned proximate a top portion of the side wall.

14. The sensor arrangement of claim 12, wherein the piston is moveable between a first position in which the piston blocks the first port such that sensor calibration fluid is inhibited from entering the chamber through the first port, and a second position in which the first port is open and sensor calibration fluid can enter the chamber through the first port.

15. The sensor arrangement of claim 12, wherein the piston includes a blocking portion for blocking the first port, the blocking portion having a length that is at least as long as a maximum stroke length of the piston.

16. The sensor arrangement of claim 12, wherein the piston is adapted to force sensor calibration fluid out of the chamber through the second port, and the piston covers the first port when sensor calibration fluid is being forced through the second port by the piston.

17. The sensor arrangement of claim 1, further comprising a controller for causing the springe to draw the blood sample through the first flow line and past the lactate sensor at a flow rate less than 50 microliters per minute.

18. The sensor arrangement of claim 1, wherein the calibration fluid also includes an anticoagulant.

19. The sensor arrangement of claim 1, wherein the calibrant includes lactate.

20. The sensor arrangement of claim 1, further comprising a controller for automatically drawing fluid samples at pre-set times and testing the samples for lactate.

21. The sensor arrangement of claim 20, wherein the fluid samples are drawn at predetermined time intervals.

22. The sensor arrangement of claim 20, wherein lactate readings generated by the lactate sensor are stored in memory associated with the controller.

23. A sensor arrangement comprising:

a sensor;

a syringe including a syringe housing defining a piston chamber having a longitudinal axis and a piston mounted within the chamber, the piston being reciprocally moveable within the chamber along the longitudinal axis, the syringe housing defining first and second ports that provide access to the piston chamber, the first port being spaced from the second port in a direction extending generally along the longitudinal axis;

a first fluid flow line providing fluid communication between the sensor and a sample fluid;

a second fluid flow line providing fluid communication between the second port of the syringe housing and the sensor; and a source of calibrant solution including calibrant for calibrating the sensor, the source of calibrant solution being in fluid communication with the first port of the syringe housing.

24. The sensor arrangement of claim 23, wherein the first and second fluid flow lines form at least portions of a valveless flow path extending from the sample fluid, past the sensor, to the second port of the syringe.

25. The sensor arrangement of claim 24, wherein when the piston is moved in a first direction relative to the syringe housing, calibrant solution is forced out the second port into the second flow line and past the sensor thereby allowing the sensor to be calibrated, and when the piston is moved in a second direction relative to the syringe housing, sample fluid is drawn through the medical device into the first flow line and past the sensor thereby allowing the sample fluid to be tested by the sensor.

26. The sensor arrangement of claim 23, wherein the syringe housing includes a first end portion positioned opposite from a second end portion, and a side wall extending between the first and second end portions, the first port being defined by the side wall and the second port being defined by one of the first and second end portions of the housing.

27. The sensor arrangement of claim 26, wherein the first port extends in a radial direction relative to the longitudinal axis, and the second port extends in an axial direction relative to the longitudinal axis.

28. The sensor arrangement of claim 23, wherein the piston is moveable between a first position in which the piston blocks the first port such that calibration solution is inhibited from entering the chamber through the first port, and a second position in which the first port is open and the calibration solution can enter the chamber through the first port.

29. The sensor arrangement of claim 23, wherein the piston includes a blocking portion for blocking the first port, the blocking portion having a length that is at least as long as a maximum stroke length of the piston.

30. The sensor arrangement of claim 23, wherein the piston is adapted to force calibration solution out of the chamber through the second port, and the piston covers the first port when the calibration solution is being forced through the second port by the piston.

31. The sensor arrangement of claim 23, wherein the sensor is a lactate sensor.

32. The sensor arrangement of claim 31, wherein the lactate sensor is an electrochemical sensor.

33. The sensor arrangement of claim 23, wherein first flow line is coupled to a catheter.

34. The sensor arrangement of claim 23, wherein the calibrant solution includes an anti-coagulant.

35. The sensor arrangement of claim 23, wherein the calibrant solution includes lactate.

36. A fluid control device comprising:

a housing defining a piston chamber having a longitudinal axis, the housing defining first and second ports that provide access to the piston chamber, the first port being spaced from the second port in a direction generally along the longitudinal axis; and a piston mounted within the piston chamber and reciprocally moveable along the longitudinal axis, the piston including a blocking portion for blocking and unblocking the first port, the blocking portion having a length that is at least as long as a maximum stroke length of the piston, the maximum stroke length of the piston being measured from a top of the first port to a farthest point the piston penetrates within the piston chamber.

37. The fluid control device of claim 36, wherein the housing includes a first end portion positioned opposite from a second end portion, and a side wall extending between the first and second end portions, the first port being defined by the side wall and the second port being defined by one of the first and second end portions of the housing.

38. The fluid control device of claim 37, wherein the first port extends in a radial direction relative to the longitudinal axis, and the second port extends in an axial direction relative to the longitudinal axis.

39. The sensor arrangement of claim 1, further comprising a controller for causing the springe to draw the blood sample through the first flow line and past the lactate sensor at a flow rate less than 100 microliters per minute.

* * * * *

UNITED STATES PATENT AND TRADEMARK OFFICE
CERTIFICATE OF CORRECTION

PATENT NO.    : 6,117,290
DATED         : September 12, 2000
INVENTOR(S)   : Say et al.

It is certified that error appears in the above-identified patent and that said Letters Patent is hereby corrected as shown below:

<u>Column 17,</u>
Line 58, "springe" should read -- syringe --

<u>Column 20,</u>
Line 15, "springe" should read -- syringe --

Signed and Sealed this

Nineteenth Day of August, 2003

JAMES E. ROGAN
*Director of the United States Patent and Trademark Office*